(12) United States Patent
Lant

(10) Patent No.: US 10,550,443 B2
(45) Date of Patent: Feb. 4, 2020

(54) CLEANING COMPOSITIONS INCLUDING ENZYMES

(71) Applicant: The Procter & Gamble Company, Cincinnati, OH (US)

(72) Inventor: Neil Joseph Lant, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/826,985

(22) Filed: Nov. 30, 2017

(65) Prior Publication Data

US 2018/0155802 A1 Jun. 7, 2018

(30) Foreign Application Priority Data

Dec. 2, 2016 (EP) .................................... 16202069
Dec. 2, 2016 (EP) .................................... 16202070

(51) Int. Cl.
*C12N 9/96* (2006.01)
*C12R 1/38* (2006.01)
*C11D 17/04* (2006.01)
*C11D 3/386* (2006.01)

(52) U.S. Cl.
CPC ............ *C12Y 302/01* (2013.01); *C11D 3/386* (2013.01); *C11D 17/04* (2013.01); *C12R 1/38* (2013.01)

(58) Field of Classification Search
None
See application file for complete search history.

(56) References Cited

U.S. PATENT DOCUMENTS

| | | | |
|---|---|---|---|
| 4,760,025 A | 7/1988 | Estell et al. |
| 5,035,661 A | 7/1991 | Steinhardt et al. |
| 5,352,604 A | 10/1994 | Wilson et al. |
| 5,679,630 A | 10/1997 | Baeck et al. |
| 5,763,385 A | 6/1998 | Bott et al. |
| 5,824,532 A | 10/1998 | Barnett et al. |
| 5,856,164 A | 1/1999 | Outtrup et al. |
| 5,989,169 A | 11/1999 | Svendsen et al. |
| 6,093,562 A | 7/2000 | Bisgard et al. |
| 6,204,232 B1 | 3/2001 | Borchert et al. |
| 6,297,038 B1 | 10/2001 | Bisgård-Frantzen et al. |
| 6,312,936 B1 | 11/2001 | Poulise et al. |
| 6,403,355 B1 | 6/2002 | Hagihara et al. |
| 6,514,926 B1 | 2/2003 | Kott et al. |
| 6,583,096 B1 | 6/2003 | Kott et al. |
| 6,638,748 B2 | 10/2003 | Hatada et al. |
| 6,939,702 B1 | 9/2005 | Vind et al. |
| 7,141,403 B2 | 11/2006 | Outtrup et al. |
| 7,262,042 B2 | 8/2007 | Weber et al. |
| 8,084,240 B2 | 12/2011 | Cuevas et al. |
| 8,114,656 B2 | 2/2012 | Shaw et al. |
| 8,236,545 B2 | 8/2012 | Cascao-Pereira et al. |
| 8,535,927 B1 | 9/2013 | Jones et al. |
| 8,716,208 B2 | 5/2014 | Meek et al. |
| 8,753,861 B2 | 6/2014 | Cascao-Pereira et al. |
| 8,785,171 B2 | 7/2014 | Souter et al. |
| 8,852,912 B2 | 10/2014 | Estell et al. |
| 9,404,070 B2 | 8/2016 | Lant et al. |
| 9,493,730 B2 | 11/2016 | Meek et al. |
| 9,670,436 B2 | 6/2017 | Jackson et al. |
| 2003/0203466 A1 | 10/2003 | Kauppinen et al. |
| 2008/0193999 A1 | 8/2008 | Andersen et al. |
| 2009/0176680 A1* | 7/2009 | Patterson ............ C11D 3/38645 510/300 |
| 2009/0217464 A1 | 9/2009 | Souter et al. |
| 2010/0125047 A1* | 5/2010 | Lant ....................... C11D 3/222 510/320 |
| 2010/0192985 A1 | 8/2010 | Wolfgang et al. |
| 2010/0240571 A1 | 9/2010 | Boutique et al. |
| 2011/0023487 A1 | 2/2011 | Olia |
| 2011/0251073 A1 | 10/2011 | Cascao-Pereira et al. |
| 2012/0135498 A1 | 5/2012 | Greiner-Stoeffele et al. |
| 2013/0260438 A1 | 10/2013 | Alekseyev et al. |
| 2014/0066353 A1 | 3/2014 | Wang et al. |
| 2014/0135252 A1 | 5/2014 | Jones et al. |
| 2014/0296127 A1 | 10/2014 | Hulskotter et al. |
| 2015/0125925 A1 | 5/2015 | Souter et al. |
| 2016/0066575 A1 | 3/2016 | Hatzelt et al. |
| 2017/0183643 A1 | 6/2017 | Krogh et al. |
| 2017/0216410 A1* | 8/2017 | Howell .................. A01N 63/04 |
| 2018/0042243 A1* | 2/2018 | Ma ......................... A01N 43/60 |

FOREIGN PATENT DOCUMENTS

| | | |
|---|---|---|
| EP | 1059351 A1 | 12/2000 |
| WO | WO8906270 | 7/1989 |
| WO | WO9108281 | 7/1991 |
| WO | WO9402597 | 2/1994 |
| WO | 9905082 | 2/1999 |
| WO | 9905084 | 2/1999 |

(Continued)

OTHER PUBLICATIONS

U.S. Appl. No. 15/827,021, filed Nov. 30, 2017, Neil Joseph Lant.
European Search Report for appl. No. 16202069.7-1358, dated Mar. 16, 2017, 6 pages.
European Search Report for appl. No. 16202070.5-1358, dated Mar. 24, 2017, 7 pages.
Extended EP Search Report for application No. 17204716.9-1106, Jan. 22, 2018, 6 pages, EP.

*Primary Examiner* — Hope A Robinson

(74) *Attorney, Agent, or Firm* — Andres E. Velarde; Melissa G. Krasovec

(57) ABSTRACT

Cleaning compositions having an amylase enzyme and a glycosyl hydrolase enzyme. Methods of making and using cleaning compositions having an amylase enzyme and a glycosyl hydrolase enzyme.

16 Claims, No Drawings

Specification includes a Sequence Listing.

(56) References Cited

FOREIGN PATENT DOCUMENTS

| WO | 9905241 | 2/1999 |
|---|---|---|
| WO | WO9905241 A1 | 2/1999 |
| WO | WO9905242 A1 | 2/1999 |
| WO | WO9905243 A1 | 2/1999 |
| WO | WO9905244 A1 | 2/1999 |
| WO | WO0060060 | 10/2000 |
| WO | WO2008087497 | 7/2008 |
| WO | WO2009021867 | 2/2009 |
| WO | WO2012080088 A1 | 6/2012 |
| WO | WO2015040159 A3 | 10/2015 |
| WO | WO2015184526 A1 | 12/2015 |
| WO | WO2015185689 | 12/2015 |
| WO | WO2016079045 A1 | 5/2016 |
| WO | WO2016090472 A1 | 6/2016 |
| WO | WO2016110379 A1 | 7/2016 |

\* cited by examiner

SEQUENCE LISTING

<160> NUMBER OF SEQ ID NOS: 32

<210> SEQ ID NO 1
<211> LENGTH: 257
<212> TYPE: PRT
<213> ORGANISM: Pseudomonas aeruginosa

<400> SEQUENCE: 1

Gly Gly Pro Ser Ser Val Ala Phe Trp Tyr Ala Glu Arg Pro Pro Leu
1               5                   10                  15

Ala Glu Leu Ser Gln Phe Asp Trp Val Val Leu Glu Ala Ala His Leu
            20                  25                  30

Lys Pro Ala Asp Val Gly Tyr Leu Lys Glu Gln Gly Ser Thr Pro Phe
        35                  40                  45

Ala Tyr Leu Ser Val Gly Glu Phe Asp Gly Asp Ala Ala Ile Ala
    50                  55                  60

Asp Ser Gly Leu Ala Arg Gly Lys Ser Ala Val Arg Asn Gln Ala Trp
65                  70                  75                  80

Asn Ser Gln Val Met Asp Leu Ala Ala Pro Ser Trp Arg Ala His Leu
                85                  90                  95

Leu Lys Arg Ala Ala Glu Leu Arg Lys Gln Gly Tyr Ala Gly Leu Phe
            100                 105                 110

Leu Asp Thr Leu Asp Ser Phe Gln Leu Gln Ala Glu Gly Arg Arg Glu
            115                 120                 125

Gly Gln Arg Arg Ala Leu Ala Ser Phe Leu Ala Gln Leu His Arg Gln
        130                 135                 140

Glu Pro Gly Leu Lys Leu Phe Phe Asn Arg Gly Phe Glu Val Leu Pro
145                 150                 155                 160

Glu Leu Pro Gly Val Ala Ser Ala Val Ala Val Glu Ser Ile His Ala
                165                 170                 175

Gly Trp Asp Ala Ala Gly Gln Tyr Arg Glu Val Pro Gln Asp Asp
            180                 185                 190

Arg Asp Trp Leu Lys Gly His Leu Asp Ala Leu Arg Ala Gln Gly Met
        195                 200                 205

Pro Ile Val Ala Ile Asp Tyr Leu Pro Pro Glu Arg Arg Asp Glu Ala
    210                 215                 220

Arg Ala Leu Ala Ala Arg Leu Arg Ser Glu Gly Tyr Val Pro Phe Val
225                 230                 235                 240

Ser Thr Pro Ala Leu Asp Tyr Leu Gly Val Ser Asp Val Glu Val Gln
                245                 250                 255

Pro

<210> SEQ ID NO 2
<211> LENGTH: 480
<212> TYPE: PRT
<213> ORGANISM: B. licheniformis

<400> SEQUENCE: 2

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

-continued

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Trp Ile Asn His Lys Gly Ala Asp Ala Thr Glu
            100                 105                 110

Asp Val Thr Ala Val Glu Val Asp Pro Ala Asp Arg Asn Arg Val Ile
            115                 120                 125

Ser Gly Glu His Leu Ile Lys Ala Trp Thr His Phe His Phe Pro Gly
            130                 135                 140

Arg Gly Ser Thr Tyr Ser Asp Phe Lys Trp His Trp Tyr His Phe Asp
145                 150                 155                 160

Gly Thr Asp Trp Asp Glu Ser Arg Lys Leu Asn Arg Ile Tyr Lys Phe
            165                 170                 175

Gln Gly Lys Ala Trp Asp Trp Glu Val Ser Asn Glu Asn Gly Asn Tyr
            180                 185                 190

Asp Tyr Leu Met Tyr Ala Asp Ile Asp Tyr Asp His Pro Asp Val Ala
            195                 200                 205

Ala Glu Ile Lys Arg Trp Gly Thr Trp Tyr Ala Asn Glu Leu Gln Leu
210                 215                 220

Asp Gly Phe Arg Leu Asp Ala Val Lys His Ile Lys Phe Ser Phe Leu
225                 230                 235                 240

Arg Asp Trp Val Asn His Val Arg Glu Lys Thr Gly Lys Glu Met Phe
            245                 250                 255

Thr Val Ala Glu Tyr Trp Gln Asn Asp Leu Gly Ala Leu Glu Asn Tyr
            260                 265                 270

Leu Asn Lys Thr Asn Phe Asn His Ser Val Phe Asp Val Pro Leu His
            275                 280                 285

Tyr Gln Phe His Ala Ala Ser Thr Gln Gly Gly Tyr Asp Met Arg
290                 295                 300

Lys Leu Leu Asn Gly Thr Trp Ser Lys His Pro Leu Lys Ser Val Thr
305                 310                 315                 320

Phe Val Asp Asn His Asp Thr Gln Pro Gly Gln Ser Leu Glu Ser Thr
            325                 330                 335

Val Gln Thr Trp Phe Lys Pro Leu Ala Tyr Ala Phe Ile Leu Thr Arg
            340                 345                 350

Glu Ser Gly Tyr Pro Gln Val Phe Tyr Gly Asp Met Tyr Gly Thr Lys
            355                 360                 365

Gly Asp Ser Gln Arg Glu Ile Pro Ala Leu Lys His Lys Ile Glu Pro
            370                 375                 380

Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Asp Ser Ser
            405                 410                 415

Val Ala Asn Ser Gly Leu Ala Ala Leu Ile Thr Asp Gly Pro Gly Gly
            420                 425                 430

Ala Lys Arg Met Tyr Val Gly Arg Gln Asn Ala Gly Glu Thr Trp His
            435                 440                 445

Asp Ile Thr Gly Asn Arg Ser Glu Pro Trp Ile Asn Ser Glu Gly Trp
            450                 455                 460

Gly Glu Phe His Val Asn Gly Gly Ser Val Ser Ile Tyr Val Gln Arg
465                 470                 475                 480

<210> SEQ ID NO 3
<211> LENGTH: 485
<212> TYPE: PRT
<213> ORGANISM: Bacillus sp.

<400> SEQUENCE: 3

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
370                 375                 380

```
Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
        420                 425                 430

Gly Ala Gly Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
        450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 4
<211> LENGTH: 485
<212> TYPE: PRT
<213> ORGANISM: Bacillus sp.

<400> SEQUENCE: 4

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
            85                  90                  95

Val Gln Val Tyr Gly Asp Val Val Met Asn His Lys Gly Gly Ala Asp
        100                 105                 110

Ala Thr Glu Asn Val Leu Ala Val Glu Val Asn Pro Asn Asn Arg Asn
    115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
```

```
            260                 265                 270
Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
    290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
    450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 5
<211> LENGTH: 484
<212> TYPE: PRT
<213> ORGANISM: Bacillus sp.

<400> SEQUENCE: 5

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140
```

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
            165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
            195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
            275                 280                 285

Phe Asp Val Pro Leu His Tyr Asn Leu Tyr Asn Ala Ser Lys Ser Gly
290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
            325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Gly Trp Thr Arg Glu Gly
            405                 410                 415

Asn Thr Ala His Pro Asn Ser Gly Leu Ala Thr Ile Met Ser Asp Gly
            420                 425                 430

Ala Gly Gly Ser Lys Trp Met Phe Val Gly Arg Asn Lys Ala Gly Gln
            435                 440                 445

Val Trp Ser Asp Ile Thr Gly Asn Arg Thr Gly Thr Val Thr Ile Asn
450                 455                 460

Ala Asp Gly Trp Gly Asn Phe Ser Val Asn Gly Gly Ser Val Ser Ile
465                 470                 475                 480

Trp Val Asn Lys

<210> SEQ ID NO 6
<211> LENGTH: 515
<212> TYPE: PRT
<213> ORGANISM: Geobacillus Stearophermophilus

<400> SEQUENCE: 6

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

-continued

```
Leu Ser Ser Leu Gly Ile Thr Ala Leu Trp Leu Pro Ala Tyr Lys
         35                  40                  45
Gly Thr Ser Arg Ser Asp Val Gly Tyr Gly Val Tyr Asp Leu Tyr Asp
     50                  55                  60
Leu Gly Glu Phe Asn Gln Lys Gly Thr Val Arg Thr Lys Tyr Gly Thr
 65                  70                  75                  80
Lys Ala Gln Tyr Leu Gln Ala Ile Gln Ala His Ala Ala Gly Met
                 85                  90                  95
Gln Val Tyr Ala Asp Val Val Phe Asp His Lys Gly Ala Asp Gly
             100                 105                 110
Thr Glu Trp Val Asp Ala Val Glu Val Asn Pro Ser Asp Arg Asn Gln
         115                 120                 125
Glu Ile Ser Gly Thr Tyr Gln Ile Gln Ala Trp Thr Lys Phe Asp Phe
     130                 135                 140
Pro Gly Arg Gly Asn Thr Tyr Ser Ser Phe Lys Trp Arg Trp Tyr His
145                 150                 155                 160
Phe Asp Gly Val Asp Trp Asp Glu Ser Arg Lys Leu Ser Arg Ile Tyr
                 165                 170                 175
Lys Phe Arg Gly Ile Gly Lys Ala Trp Asp Trp Glu Val Asp Thr Glu
             180                 185                 190
Asn Gly Asn Tyr Asp Tyr Leu Met Tyr Ala Asp Leu Asp Met Asp His
         195                 200                 205
Pro Glu Val Val Thr Glu Leu Lys Asn Trp Gly Lys Trp Tyr Val Asn
     210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Tyr Val Arg Ser Gln Thr Gly
                 245                 250                 255
Lys Pro Leu Phe Thr Val Gly Glu Tyr Trp Ser Tyr Asp Ile Asn Lys
             260                 265                 270
Leu His Asn Tyr Ile Thr Lys Thr Asn Gly Thr Met Ser Leu Phe Asp
         275                 280                 285
Ala Pro Leu His Asn Lys Phe Tyr Thr Ala Ser Lys Ser Gly Gly Ala
     290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                 325                 330                 335
Ala Leu Gln Ser Trp Val Asp Pro Trp Phe Lys Pro Leu Ala Tyr Ala
             340                 345                 350
Phe Ile Leu Thr Arg Gln Glu Gly Tyr Pro Cys Val Phe Tyr Gly Asp
         355                 360                 365
Tyr Tyr Gly Ile Pro Gln Tyr Asn Ile Pro Ser Leu Lys Ser Lys Ile
     370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                 405                 410                 415
Thr Glu Lys Pro Gly Ser Gly Leu Ala Ala Leu Ile Thr Asp Gly Pro
             420                 425                 430
Gly Gly Ser Lys Trp Met Tyr Val Gly Lys Gln His Ala Gly Lys Val
         435                 440                 445
Phe Tyr Asp Leu Thr Gly Asn Arg Ser Asp Thr Val Thr Ile Asn Ser
```

```
            450                 455                 460
Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
                500                 505                 510

Ala Trp Pro
        515

<210> SEQ ID NO 7
<211> LENGTH: 485
<212> TYPE: PRT
<213> ORGANISM: Geobacillus Stearophermophilus

<400> SEQUENCE: 7

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
        50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Gly Lys Ala Trp Asp Trp Glu Val Asp Thr Glu Asn
            180                 185                 190

Gly Asn Tyr Asp Tyr Leu Met Tyr Ala Asp Leu Asp Met Asp His Pro
        195                 200                 205

Glu Val Val Thr Glu Leu Lys Asn Trp Gly Lys Trp Tyr Val Asn Thr
    210                 215                 220

Thr Asn Ile Asp Gly Phe Arg Leu Asp Ala Val Lys His Ile Lys Phe
225                 230                 235                 240

Ser Phe Phe Pro Asp Trp Leu Ser Tyr Val Arg Ser Gln Thr Gly Lys
                245                 250                 255

Pro Leu Phe Thr Val Gly Glu Tyr Trp Ser Tyr Asp Ile Asn Lys Leu
            260                 265                 270

His Asn Tyr Ile Thr Lys Thr Asn Gly Thr Met Ser Leu Phe Asp Ala
        275                 280                 285

Pro Leu His Asn Lys Phe Tyr Thr Ala Ser Lys Ser Gly Gly Ala Phe
    290                 295                 300
```

```
Asp Met Arg Thr Leu Met Thr Asn Thr Leu Met Lys Asp Gln Pro Thr
305                 310                 315                 320

Leu Ala Val Thr Phe Val Asp Asn His Asp Thr Glu Pro Gly Gln Ala
            325                 330                 335

Leu Gln Ser Trp Val Asp Pro Trp Phe Lys Pro Leu Ala Tyr Ala Phe
        340                 345                 350

Ile Leu Thr Arg Gln Glu Gly Tyr Pro Cys Val Phe Tyr Gly Asp Tyr
    355                 360                 365

Tyr Gly Ile Pro Gln Tyr Asn Ile Pro Ser Leu Lys Ser Lys Ile Asp
370                 375                 380

Pro Leu Leu Ile Ala Arg Arg Asp Tyr Ala Tyr Gly Thr Gln His Asp
385                 390                 395                 400

Tyr Leu Asp His Ser Asp Ile Ile Gly Trp Thr Arg Glu Gly Val Thr
            405                 410                 415

Glu Lys Pro Gly Ser Gly Leu Ala Ala Leu Ile Thr Asp Gly Pro Gly
        420                 425                 430

Gly Ser Lys Trp Met Tyr Val Gly Lys Gln His Ala Gly Lys Val Phe
    435                 440                 445

Tyr Asp Leu Thr Gly Asn Arg Ser Asp Thr Val Thr Ile Asn Ser Asp
450                 455                 460

Gly Trp Gly Glu Phe Lys Val Asn Gly Gly Ser Val Ser Val Trp Val
465                 470                 475                 480

Pro Arg Lys Thr Thr
            485

<210> SEQ ID NO 8
<211> LENGTH: 483
<212> TYPE: PRT
<213> ORGANISM: Artificial
<220> FEATURE:
<223> OTHER INFORMATION: WO2016091688

<400> SEQUENCE: 8

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
            85                  90                  95

Ile Gln Val Tyr Gly Asp Val Val Met Asn His Lys Gly Gly Ala Asp
        100                 105                 110

Ala Thr Glu Met Val Arg Ala Val Glu Val Asn Pro Asn Asn Arg Asn
    115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
            165                 170                 175
```

Ile Tyr Lys Phe Arg Gly Lys Ala Trp Asp Trp Glu Val Asp Thr Glu
            180                 185                 190

Asn Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Gln Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Asn Ile Phe Asn Gly Thr Val Val Gln Arg His Pro
305                 310                 315                 320

Ser His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365

Tyr Tyr Gly Ile Pro Thr His Gly Val Pro Ala Met Arg Ser Lys Ile
    370                 375                 380

Asp Pro Ile Leu Glu Ala Arg Gln Lys Tyr Ala Tyr Gly Pro Gln His
385                 390                 395                 400

Asp Tyr Leu Asp His Pro Asp Val Ile Gly Trp Thr Arg Glu Gly Asp
                405                 410                 415

Ser Ser His Pro Lys Ser Gly Leu Ala Thr Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 9
<211> LENGTH: 480
<212> TYPE: PRT
<213> ORGANISM: Paenibacillus curdlanolyticus

<400> SEQUENCE: 9

Ala Asp Asn Gly Thr Ile Met Gln Tyr Phe Glu Trp Tyr Leu Pro Asn
1               5                   10                  15

Asp Gly Ala His Trp Asn Arg Leu Asn Asn Asp Ala Gln Asn Leu Lys
            20                  25                  30

Asn Val Gly Ile Thr Ala Val Trp Ile Pro Pro Ala Tyr Lys Gly Gly
        35                  40                  45

Ser Ser Ala Asp Val Gly Tyr Gly Val Tyr Asp Thr Tyr Asp Leu Gly
    50                  55                  60

```
Glu Phe Asn Gln Lys Gly Thr Val Arg Thr Lys Tyr Gly Thr Lys Ser
 65                  70                  75                  80

Glu Leu Ile Ser Ala Val Asn Asn Leu His Ala Lys Gly Ile Ala Val
                 85                  90                  95

Tyr Gly Asp Val Val Leu Asn His Arg Met Asn Ala Asp Ala Thr Glu
            100                 105                 110

Leu Val Asp Ala Val Glu Val Asp Pro Asn Asn Arg Asn Val Glu Thr
        115                 120                 125

Thr Ser Thr Tyr Gln Ile Gln Ala Trp Thr Gln Tyr Asp Phe Pro Gly
    130                 135                 140

Arg Gly Asn Thr Tyr Ser Ser Phe Lys Trp Arg Trp Tyr His Phe Asp
145                 150                 155                 160

Gly Val Asp Trp Asp Gln Ser Arg Gly Leu Asn Arg Ile Tyr Lys Leu
                165                 170                 175

Arg Gly Asp Gly Lys Asp Trp Asp Trp Glu Val Asp Ser Glu Tyr Gly
            180                 185                 190

Asn Tyr Asp Tyr Leu Met Gly Ala Asp Leu Asp Phe Asn His Pro Asp
        195                 200                 205

Val Val Asn Glu Thr Lys Thr Trp Gly Lys Trp Phe Val Asn Thr Val
    210                 215                 220

Asn Leu Asp Gly Val Arg Leu Asp Ala Val Lys His Ile Lys Phe Asp
225                 230                 235                 240

Phe Met Arg Asp Trp Val Asn Asn Val Arg Ser Thr Thr Gly Lys Asn
                245                 250                 255

Leu Phe Ala Val Gly Glu Tyr Trp His Tyr Asp Val Asn Lys Leu Asn
            260                 265                 270

Ser Tyr Ile Thr Lys Thr Asn Gly Thr Met Ser Leu Phe Asp Val Pro
        275                 280                 285

Leu His Phe Arg Phe Tyr Asp Ala Ser Asn Gly Gly Gly Tyr Asp
    290                 295                 300

Met Arg Asn Leu Leu Asn Asn Thr Leu Met Ser Ser Asn Pro Met Lys
305                 310                 315                 320

Ala Val Thr Phe Val Glu Asn His Asp Thr Gln Pro Thr Gln Ala Leu
                325                 330                 335

Gln Ser Thr Val Gln Ser Trp Phe Lys Pro Leu Ala Tyr Ala Thr Ile
            340                 345                 350

Leu Thr Arg Glu Gln Gly Tyr Pro Cys Val Phe Tyr Gly Asp Tyr Tyr
        355                 360                 365

Gly Thr Ser Asp Gly Lys Ile Ser Ser Tyr Lys Pro Ile Met Asp Lys
    370                 375                 380

Leu Leu Asn Ala Arg Lys Val Tyr Ala Tyr Gly Thr Gln Arg Asp Tyr
385                 390                 395                 400

Phe Asp His Pro Asp Ile Val Gly Trp Thr Arg Glu Gly Asp Ala Ala
                405                 410                 415

His Ala Gly Ser Gly Leu Ala Thr Leu Ile Thr Asp Gly Pro Gly Gly
            420                 425                 430

Ser Lys Trp Met Tyr Val Gly Thr Ser Lys Ala Gly Gln Val Trp Thr
        435                 440                 445

Asp Lys Thr Gly Asn Arg Ser Gly Thr Val Thr Ile Asp Ala Asn Gly
    450                 455                 460

Trp Gly Asn Phe Trp Val Asn Gly Gly Ser Val Ser Val Trp Ala Lys
465                 470                 475                 480
```

<210> SEQ ID NO 10
<211> LENGTH: 483
<212> TYPE: PRT
<213> ORGANISM: Cytophaga sp.

<400> SEQUENCE: 10

| Ala | Ala | Thr | Asn | Gly | Thr | Met | Met | Gln | Tyr | Phe | Glu | Trp | Tyr | Val | Pro |
|---|---|---|---|---|---|---|---|---|---|---|---|---|---|---|---|
| 1 | | | | 5 | | | | | 10 | | | | | 15 | |

| Asn | Asp | Gly | Gln | Gln | Trp | Asn | Arg | Leu | Arg | Thr | Asp | Ala | Pro | Tyr | Leu |
|---|---|---|---|---|---|---|---|---|---|---|---|---|---|---|---|
| | | | 20 | | | | | 25 | | | | | 30 | | |

| Ser | Ser | Val | Gly | Ile | Thr | Ala | Val | Trp | Thr | Pro | Pro | Ala | Tyr | Lys | Gly |
|---|---|---|---|---|---|---|---|---|---|---|---|---|---|---|---|
| | | | 35 | | | | | 40 | | | | | 45 | | |

| Thr | Ser | Gln | Ala | Asp | Val | Gly | Tyr | Gly | Pro | Tyr | Asp | Leu | Tyr | Asp | Leu |
|---|---|---|---|---|---|---|---|---|---|---|---|---|---|---|---|
| | 50 | | | | | 55 | | | | | 60 | | | | |

| Gly | Glu | Phe | Asn | Gln | Lys | Gly | Thr | Val | Arg | Thr | Lys | Tyr | Gly | Thr | Lys |
|---|---|---|---|---|---|---|---|---|---|---|---|---|---|---|---|
| 65 | | | | | 70 | | | | | 75 | | | | | 80 |

| Gly | Glu | Leu | Lys | Ser | Ala | Val | Asn | Thr | Leu | His | Ser | Asn | Gly | Ile | Gln |
|---|---|---|---|---|---|---|---|---|---|---|---|---|---|---|---|
| | | | | 85 | | | | | 90 | | | | | 95 | |

| Val | Tyr | Gly | Asp | Val | Val | Met | Asn | His | Lys | Ala | Gly | Ala | Asp | Tyr | Thr |
|---|---|---|---|---|---|---|---|---|---|---|---|---|---|---|---|
| | | | 100 | | | | | 105 | | | | | 110 | | |

| Glu | Asn | Val | Thr | Ala | Val | Glu | Val | Asn | Pro | Ser | Asn | Arg | Asn | Gln | Glu |
|---|---|---|---|---|---|---|---|---|---|---|---|---|---|---|---|
| | | | 115 | | | | | 120 | | | | | 125 | | |

| Thr | Ser | Gly | Glu | Tyr | Asn | Ile | Gln | Ala | Trp | Thr | Gly | Phe | Asn | Phe | Pro |
|---|---|---|---|---|---|---|---|---|---|---|---|---|---|---|---|
| | 130 | | | | | 135 | | | | | 140 | | | | |

| Gly | Arg | Gly | Thr | Thr | Tyr | Ser | Asn | Phe | Lys | Trp | Gln | Trp | Phe | His | Phe |
|---|---|---|---|---|---|---|---|---|---|---|---|---|---|---|---|
| 145 | | | | | 150 | | | | | 155 | | | | | 160 |

| Asp | Gly | Thr | Asp | Trp | Asp | Gln | Ser | Arg | Ser | Leu | Ser | Arg | Ile | Phe | Lys |
|---|---|---|---|---|---|---|---|---|---|---|---|---|---|---|---|
| | | | | 165 | | | | | 170 | | | | | 175 | |

| Phe | Thr | Gly | Lys | Ala | Trp | Asp | Trp | Pro | Val | Ser | Ser | Glu | Asn | Gly | Asn |
|---|---|---|---|---|---|---|---|---|---|---|---|---|---|---|---|
| | | | 180 | | | | | 185 | | | | | 190 | | |

| Tyr | Asp | Tyr | Leu | Met | Tyr | Ala | Asp | Tyr | Asp | Tyr | Asp | His | Pro | Asp | Val |
|---|---|---|---|---|---|---|---|---|---|---|---|---|---|---|---|
| | | | 195 | | | | | 200 | | | | | 205 | | |

| Val | Asn | Glu | Met | Lys | Lys | Trp | Gly | Val | Trp | Tyr | Ala | Asn | Glu | Val | Gly |
|---|---|---|---|---|---|---|---|---|---|---|---|---|---|---|---|
| | 210 | | | | | 215 | | | | | 220 | | | | |

| Leu | Asp | Gly | Tyr | Arg | Leu | Asp | Ala | Val | Lys | His | Ile | Lys | Phe | Ser | Phe |
|---|---|---|---|---|---|---|---|---|---|---|---|---|---|---|---|
| 225 | | | | | 230 | | | | | 235 | | | | | 240 |

| Leu | Lys | Asp | Trp | Val | Asp | Asn | Ala | Arg | Ala | Ala | Thr | Gly | Lys | Glu | Met |
|---|---|---|---|---|---|---|---|---|---|---|---|---|---|---|---|
| | | | | 245 | | | | | 250 | | | | | 255 | |

| Phe | Thr | Val | Gly | Glu | Tyr | Trp | Gln | Asn | Asp | Leu | Gly | Ala | Leu | Asn | Asn |
|---|---|---|---|---|---|---|---|---|---|---|---|---|---|---|---|
| | | | 260 | | | | | 265 | | | | | 270 | | |

| Tyr | Leu | Ala | Lys | Val | Asn | Tyr | Asn | Gln | Ser | Leu | Phe | Asp | Ala | Pro | Leu |
|---|---|---|---|---|---|---|---|---|---|---|---|---|---|---|---|
| | | 275 | | | | | 280 | | | | | 285 | | | |

| His | Tyr | Asn | Phe | Tyr | Ala | Ala | Ser | Thr | Gly | Gly | Gly | Tyr | Tyr | Asp | Met |
|---|---|---|---|---|---|---|---|---|---|---|---|---|---|---|---|
| | 290 | | | | | 295 | | | | | 300 | | | | |

| Arg | Asn | Ile | Leu | Asn | Asn | Thr | Leu | Val | Ala | Ser | Asn | Pro | Thr | Lys | Ala |
|---|---|---|---|---|---|---|---|---|---|---|---|---|---|---|---|
| 305 | | | | | 310 | | | | | 315 | | | | | 320 |

| Val | Thr | Leu | Val | Glu | Asn | His | Asp | Thr | Gln | Pro | Gly | Gln | Ser | Leu | Glu |
|---|---|---|---|---|---|---|---|---|---|---|---|---|---|---|---|
| | | | | 325 | | | | | 330 | | | | | 335 | |

| Ser | Thr | Val | Gln | Pro | Trp | Phe | Lys | Pro | Leu | Ala | Tyr | Ala | Phe | Ile | Leu |
|---|---|---|---|---|---|---|---|---|---|---|---|---|---|---|---|
| | | | 340 | | | | | 345 | | | | | 350 | | |

| Thr | Arg | Ser | Gly | Gly | Tyr | Pro | Ser | Val | Phe | Tyr | Gly | Asp | Met | Tyr | Gly |
|---|---|---|---|---|---|---|---|---|---|---|---|---|---|---|---|
| | | 355 | | | | | 360 | | | | | 365 | | | |

| Thr | Lys | Gly | Thr | Thr | Thr | Arg | Glu | Ile | Pro | Ala | Leu | Lys | Ser | Lys | Ile |
|---|---|---|---|---|---|---|---|---|---|---|---|---|---|---|---|
| | 370 | | | | | 375 | | | | | 380 | | | | |

```
Glu Pro Leu Leu Lys Ala Arg Lys Asp Tyr Ala Tyr Gly Thr Gln Arg
385                 390                 395                 400

Asp Tyr Ile Asp Asn Pro Asp Val Ile Gly Trp Thr Arg Glu Gly Asp
            405                 410                 415

Ser Thr Lys Ala Lys Ser Gly Leu Ala Thr Val Ile Thr Asp Gly Pro
        420                 425                 430

Gly Gly Ser Lys Arg Met Tyr Val Gly Thr Ser Asn Ala Gly Glu Ile
            435                 440                 445

Trp Tyr Asp Leu Thr Gly Asn Asn Ser Thr Lys Ile Thr Ile Gly Ser
        450                 455                 460

Asp Gly Tyr Ala Thr Phe Pro Val Asn Lys Gly Ser Val Ser Val Trp
465                 470                 475                 480

Val Gln Gln

<210> SEQ ID NO 11
<211> LENGTH: 618
<212> TYPE: PRT
<213> ORGANISM: Bacillus subtilis

<400> SEQUENCE: 11

Leu Thr Ala Pro Ser Ile Lys Ser Gly Thr Ile Leu His Ala Trp Asn
1               5                   10                  15

Trp Ser Phe Asn Thr Leu Lys His Asn Met Lys Asp Ile His Asp Ala
            20                  25                  30

Gly Tyr Thr Ala Ile Gln Thr Ser Pro Ile Asn Gln Val Lys Glu Gly
        35                  40                  45

Asn Gln Gly Asp Lys Ser Met Ser Asn Trp Tyr Trp Leu Tyr Gln Pro
50                  55                  60

Thr Ser Tyr Gln Ile Gly Asn Arg Tyr Leu Gly Thr Glu Gln Glu Phe
65                  70                  75                  80

Lys Glu Met Cys Ala Ala Ala Glu Glu Tyr Gly Ile Lys Val Ile Val
                85                  90                  95

Asp Ala Val Ile Asn His Thr Thr Ser Asp Tyr Ala Ala Ile Ser Asn
            100                 105                 110

Glu Val Lys Ser Ile Pro Asn Trp Thr His Gly Asn Thr Gln Ile Lys
        115                 120                 125

Asn Trp Ser Asp Arg Trp Asp Val Thr Gln Asn Ser Leu Leu Gly Leu
130                 135                 140

Tyr Asp Trp Asn Thr Gln Asn Thr Gln Val Gln Ser Tyr Leu Lys Arg
145                 150                 155                 160

Phe Leu Asp Arg Ala Leu Asn Asp Gly Ala Asp Gly Phe Arg Phe Asp
                165                 170                 175

Ala Ala Lys His Ile Glu Leu Pro Asp Asp Gly Ser Tyr Gly Ser Gln
            180                 185                 190

Phe Trp Pro Asn Ile Thr Asn Thr Ser Ala Glu Phe Gln Tyr Gly Glu
        195                 200                 205

Ile Leu Gln Asp Ser Ala Ser Arg Asp Ala Ala Tyr Ala Asn Tyr Met
210                 215                 220

Asp Val Thr Ala Ser Asn Tyr Gly His Ser Ile Arg Ser Ala Leu Lys
225                 230                 235                 240

Asn Arg Asn Leu Gly Val Ser Asn Ile Ser His Tyr Ala Ser Asp Val
                245                 250                 255

Ser Ala Asp Lys Leu Val Thr Trp Val Glu Ser His Asp Thr Tyr Ala
            260                 265                 270
```

Asn Asp Asp Glu Glu Ser Thr Trp Met Ser Asp Asp Ile Arg Leu
        275                 280                 285

Gly Trp Ala Val Ile Ala Ser Arg Ser Gly Ser Thr Pro Leu Phe Phe
290                 295                 300

Ser Arg Pro Glu Gly Gly Asn Gly Val Arg Phe Pro Gly Lys Ser
305                 310                 315                 320

Gln Ile Gly Asp Arg Gly Ser Ala Leu Phe Glu Asp Gln Ala Ile Thr
                325                 330                 335

Ala Val Asn Arg Phe His Asn Val Met Ala Gly Gln Pro Glu Glu Leu
                340                 345                 350

Ser Asn Pro Asn Gly Asn Asn Gln Ile Phe Met Asn Gln Arg Gly Ser
            355                 360                 365

His Gly Val Val Leu Ala Asn Ala Gly Ser Ser Val Ser Ile Asn
    370                 375                 380

Thr Ala Thr Lys Leu Pro Asp Gly Arg Tyr Asp Asn Lys Ala Gly Ala
385                 390                 395                 400

Gly Ser Phe Gln Val Asn Asp Gly Lys Leu Thr Gly Thr Ile Asn Ala
                405                 410                 415

Arg Ser Val Ala Val Leu Tyr Pro Asp Asp Ile Ala Lys Ala Pro His
                420                 425                 430

Val Phe Leu Glu Asn Tyr Lys Thr Gly Val Thr His Ser Phe Asn Asp
    435                 440                 445

Gln Leu Thr Ile Thr Leu Arg Ala Asp Ala Asn Thr Thr Lys Ala Val
    450                 455                 460

Tyr Gln Ile Asn Asn Gly Pro Glu Thr Ala Phe Lys Asp Gly Asp Gln
465                 470                 475                 480

Phe Thr Ile Gly Lys Gly Asp Pro Phe Gly Lys Thr Tyr Thr Ile Met
                485                 490                 495

Leu Lys Gly Thr Asn Ser Asp Gly Val Thr Arg Thr Glu Lys Tyr Ser
                500                 505                 510

Phe Val Lys Arg Asp Pro Ala Ser Ala Lys Thr Ile Gly Tyr Gln Asn
    515                 520                 525

Pro Asn His Trp Ser Gln Val Asn Ala Tyr Ile Tyr Lys His Asp Gly
    530                 535                 540

Ser Arg Val Ile Glu Leu Thr Gly Ser Trp Pro Gly Lys Pro Met Thr
545                 550                 555                 560

Lys Asn Ala Asp Gly Ile Tyr Thr Leu Thr Leu Pro Ala Asp Thr Asp
                565                 570                 575

Thr Thr Asn Ala Lys Val Ile Phe Asn Asn Gly Ser Ala Gln Val Pro
                580                 585                 590

Gly Gln Asn Gln Pro Gly Phe Asp Tyr Val Leu Asn Gly Leu Tyr Asn
            595                 600                 605

Asp Ser Gly Leu Ser Gly Ser Leu Pro His
            610                 615

```
<210> SEQ ID NO 12
<211> LENGTH: 480
<212> TYPE: PRT
<213> ORGANISM: Bacillus sp.

<400> SEQUENCE: 12
```

Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Ala Ala Leu
                20                  25                  30

```
Ser Asp Ala Gly Ile Thr Ala Ile Trp Ile Pro Ala Tyr Lys Gly
         35                  40                  45

Asn Ser Gln Ala Asp Val Gly Tyr Gly Ala Tyr Asp Leu Tyr Asp Leu
     50                  55                  60

Gly Glu Phe Asn Gln Lys Gly Thr Val Arg Thr Lys Tyr Gly Thr Lys
 65                  70                  75                  80

Ala Gln Leu Glu Arg Ala Ile Gly Ser Leu Lys Ser Asn Asp Ile Asn
                 85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
            115                 120                 125

Ile Ser Gly Ala Tyr Thr Ile Asp Ala Trp Thr Gly Phe Asp Phe Ser
        130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
            195                 200                 205

Gln Asp Glu Leu Lys Asp Trp Gly Ser Trp Phe Thr Asp Glu Leu Asp
        210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
            290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365

Ile Pro Asn Asp Asn Ile Ser Ala Lys Lys Asp Met Ile Asp Glu Leu
    370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
        435                 440                 445
```

```
Leu Thr Gly Asn Asn Gly Ala Ser Val Thr Ile Asn Gly Asp Gly Trp
            450                 455                 460

Gly Glu Phe Phe Thr Asn Gly Ser Val Ser Val Tyr Val Asn Gln
465                 470                 475                 480

<210> SEQ ID NO 13
<211> LENGTH: 412
<212> TYPE: PRT
<213> ORGANISM: Pseudomonas aeruginosa

<400> SEQUENCE: 13

Glu Ile Gln Val Leu Lys Ala Pro Arg Ala Val Val Trp Lys Asp Phe
1               5                   10                  15

Leu Gly Val Asn Ala Gln Phe Leu Trp Phe Ser Pro Glu Arg Tyr Asn
            20                  25                  30

Lys Gln Ile Asp Arg Leu Gln Asp Leu Gly Leu Glu Trp Val Arg Leu
        35                  40                  45

Asp Leu His Trp Asp Arg Leu Glu Thr Ala Glu Asp Gln Tyr Gln Leu
    50                  55                  60

Ala Ser Leu Asp Gln Leu Val Lys Asp Leu Glu Ala Arg Gln Leu Lys
65                  70                  75                  80

Ser Val Phe Tyr Leu Val Gly Ser Ala Arg Phe Ile Thr Thr Ala Pro
                85                  90                  95

Phe Tyr Ser Pro Phe Gln Asp Gln Tyr Pro Pro Arg Asp Pro Glu Val
            100                 105                 110

Phe Ala Arg Arg Met Ala Met Leu Ser Gln Arg Tyr Pro Ser Val Ala
        115                 120                 125

Ala Trp Gln Val Trp Asn Glu Pro Asn Leu Ile Gly Phe Trp Arg Pro
    130                 135                 140

Lys Ala Asp Pro Glu Gly Tyr Ala Lys Leu Leu Gln Ala Ser Thr Ile
145                 150                 155                 160

Ala Leu Arg Met Val Asp Pro Glu Lys Pro Val Val Ser Ala Gly Met
                165                 170                 175

Ala Phe Phe Ser Glu Met Pro Asp Gly Arg Thr Met Phe Asp Ala Leu
            180                 185                 190

Gly His Leu Gly Val Glu Ser Leu Gly Thr Ile Ala Thr Tyr His Pro
        195                 200                 205

Tyr Thr Gln Leu Pro Glu Gly Asn Tyr Pro Trp Asn Leu Asp Phe Val
    210                 215                 220

Ser His Ala Asn Gln Ile Asn Arg Ala Leu Arg Asn Ala Gly Val Pro
225                 230                 235                 240

Ala Ile Trp Ser Thr Glu Trp Gly Trp Ser Ala Tyr Lys Gly Pro Lys
                245                 250                 255

Glu Leu Gln Asp Ile Ile Gly Val Glu Gly Gln Ala Asp Tyr Val Leu
            260                 265                 270

Arg Arg Leu Ala Leu Met Ser Ala Leu Asp Tyr Asp Arg Ile Phe Leu
        275                 280                 285

Phe Thr Leu Ser Asp Leu Asp Gln Arg Ala Ser Val Arg Asp Arg Asp
    290                 295                 300

Tyr Gly Leu Leu Asp Leu Asp Ala Asn Pro Lys Pro Tyr Leu Ala
305                 310                 315                 320

Leu Gln Arg Phe Leu Lys Val Thr Gly Pro Lys Leu Arg Pro Ala Asp
                325                 330                 335

Pro Pro Val Thr Glu Asp Leu Pro Asp Gly Ser Phe Ser Ile Gly Trp
            340                 345                 350
```

Thr Arg Glu Asp Gly Arg Asn Val Trp Leu Phe Trp Ser Ala Arg Gly
        355                 360                 365

Gly Asn Val Arg Leu Pro Lys Leu Lys Glu Ala Thr Leu His Asp Pro
    370                 375                 380

Leu Ser Gly Lys Val Thr Pro Leu Ser Gly Ser Asp Gly Leu Glu Val
385                 390                 395                 400

Pro Val Lys Ser Ser Leu Gln Met Leu Val Trp Glu
                405                 410

<210> SEQ ID NO 14
<211> LENGTH: 109
<212> TYPE: PRT
<213> ORGANISM: Bacillus licheniformis

<400> SEQUENCE: 14

Ala Arg Tyr Asp Asp Val Leu Tyr Phe Pro Ala Ser Arg Tyr Pro Glu
1               5                   10                  15

Thr Gly Ala His Ile Ser Asp Ala Ile Lys Ala Gly His Ala Asp Val
            20                  25                  30

Cys Thr Ile Glu Arg Ser Gly Ala Asp Lys Arg Gln Glu Ser Leu
        35                  40                  45

Lys Gly Ile Pro Thr Lys Pro Gly Phe Asp Arg Asp Glu Trp Pro Met
    50                  55                  60

Ala Met Cys Glu Glu Gly Gly Lys Gly Ala Ser Val Arg Tyr Val Ser
65                  70                  75                  80

Ser Ser Asp Asn Arg Gly Ala Gly Ser Trp Val Gly Asn Arg Leu Asn
                85                  90                  95

Gly Tyr Ala Asp Gly Thr Arg Ile Leu Phe Ile Val Gln
            100                 105

<210> SEQ ID NO 15
<211> LENGTH: 109
<212> TYPE: PRT
<213> ORGANISM: Bacillus subtilis

<400> SEQUENCE: 15

Ala Ser Ser Tyr Asp Lys Val Leu Tyr Phe Pro Leu Ser Arg Tyr Pro
1               5                   10                  15

Glu Thr Gly Ser His Ile Arg Asp Ala Ile Ala Glu Gly His Pro Asp
            20                  25                  30

Ile Cys Thr Ile Asp Asp Gly Ala Asp Lys Arg Arg Glu Glu Ser Leu
        35                  40                  45

Lys Gly Ile Pro Thr Lys Pro Gly Tyr Asp Arg Asp Glu Trp Pro Met
    50                  55                  60

Ala Val Cys Glu Glu Gly Gly Ala Gly Ala Asp Val Arg Tyr Val Thr
65                  70                  75                  80

Pro Ser Asp Asn Arg Gly Ala Gly Ser Trp Val Gly Asn Gln Met Ser
                85                  90                  95

Ser Tyr Pro Asp Gly Thr Arg Val Leu Phe Ile Val Gln
            100                 105

<210> SEQ ID NO 16
<211> LENGTH: 109
<212> TYPE: PRT
<213> ORGANISM: Bacillus licheniformis

<400> SEQUENCE: 16

Ala Arg Tyr Asp Asp Ile Leu Tyr Phe Pro Ala Ser Arg Tyr Pro Glu
1               5                   10                  15

Thr Gly Ala His Ile Ser Asp Ala Ile Lys Ala Gly His Ser Asp Val
            20                  25                  30

Cys Thr Ile Glu Arg Ser Gly Ala Asp Lys Arg Arg Gln Glu Ser Leu
        35                  40                  45

Lys Gly Ile Pro Thr Lys Pro Gly Phe Asp Arg Asp Glu Trp Pro Met
50                  55                  60

Ala Met Cys Glu Glu Gly Lys Gly Ala Ser Val Arg Tyr Val Ser
65                  70                  75                  80

Ser Ser Asp Asn Arg Gly Ala Gly Ser Trp Val Gly Asn Arg Leu Ser
            85                  90                  95

Gly Phe Ala Asp Gly Thr Arg Ile Leu Phe Ile Val Gln
            100                 105

<210> SEQ ID NO 17
<211> LENGTH: 204
<212> TYPE: PRT
<213> ORGANISM: Aspergillus oryzae

<400> SEQUENCE: 17

Lys Thr Gly Ser Gly Asp Ser Gln Ser Asp Pro Ile Lys Ala Asp Leu
1               5                   10                  15

Glu Val Lys Gly Gln Ser Ala Leu Pro Phe Asp Val Asp Cys Trp Ala
            20                  25                  30

Ile Leu Cys Lys Gly Ala Pro Asn Val Leu Gln Arg Val Asn Glu Lys
        35                  40                  45

Thr Lys Asn Ser Asn Arg Asp Arg Ser Gly Ala Asn Lys Gly Pro Phe
50                  55                  60

Lys Asp Pro Gln Lys Trp Gly Ile Lys Ala Leu Pro Pro Lys Asn Pro
65                  70                  75                  80

Ser Trp Ser Ala Gln Asp Phe Lys Ser Pro Glu Glu Tyr Ala Phe Ala
            85                  90                  95

Ser Ser Leu Gln Gly Gly Thr Asn Ala Ile Leu Ala Pro Val Asn Leu
            100                 105                 110

Ala Ser Gln Asn Ser Gln Gly Val Leu Asn Gly Phe Tyr Ser Ala
        115                 120                 125

Asn Lys Val Ala Gln Phe Asp Pro Ser Lys Pro Gln Gln Thr Lys Gly
        130                 135                 140

Thr Trp Phe Gln Ile Thr Lys Phe Thr Gly Ala Ala Gly Pro Tyr Cys
145                 150                 155                 160

Lys Ala Leu Gly Ser Asn Asp Lys Ser Val Cys Asp Lys Asn Lys Asn
                165                 170                 175

Ile Ala Gly Asp Trp Gly Phe Pro Ala Lys Trp Ala Tyr Gln Tyr
            180                 185                 190

Asp Glu Lys Asn Asn Lys Phe Asn Tyr Val Gly Lys
        195                 200

<210> SEQ ID NO 18
<211> LENGTH: 188
<212> TYPE: PRT
<213> ORGANISM: Trichoderma harzianum

<400> SEQUENCE: 18

Ala Pro Ala Pro Met Pro Thr Pro Pro Gly Ile Pro Thr Glu Ser Ser
1               5                   10                  15

Ala Arg Thr Gln Leu Ala Gly Leu Thr Val Ala Val Ala Gly Ser Gly
                20                  25                  30

Thr Gly Tyr Ser Arg Asp Leu Phe Pro Thr Trp Asp Ala Ile Ser Gly
            35                  40                  45

Asn Cys Asn Ala Arg Glu Tyr Val Leu Lys Arg Asp Gly Glu Gly Val
        50                  55                  60

Gln Val Asn Asn Ala Cys Glu Ser Gln Ser Gly Thr Trp Ile Ser Pro
65                  70                  75                  80

Tyr Asp Asn Ala Ser Phe Thr Asn Ala Ser Ser Leu Asp Ile Asp His
                85                  90                  95

Met Val Pro Leu Lys Asn Ala Trp Ile Ser Gly Ala Ser Ser Trp Thr
            100                 105                 110

Thr Ala Gln Arg Glu Ala Leu Ala Asn Asp Val Ser Arg Pro Gln Leu
        115                 120                 125

Trp Ala Val Ser Ala Ser Ala Asn Arg Ser Lys Gly Asp Arg Ser Pro
130                 135                 140

Asp Gln Trp Lys Pro Pro Leu Thr Ser Phe Tyr Cys Thr Tyr Ala Lys
145                 150                 155                 160

Ser Trp Ile Asp Val Lys Ser Phe Tyr Lys Leu Thr Ile Thr Ser Ala
                165                 170                 175

Glu Lys Thr Ala Leu Ser Ser Met Leu Asp Thr Cys
            180                 185

<210> SEQ ID NO 19
<211> LENGTH: 458
<212> TYPE: PRT
<213> ORGANISM: Trichoderma harzianum

<400> SEQUENCE: 19

Asp Thr Thr Leu Ser Ile Asp Pro Thr Ser Asn Trp Gly Thr Trp Glu
1               5                   10                  15

Gly Trp Gly Val Ser Leu Ala Trp Trp Ala Lys Ala Phe Gly Asn Arg
                20                  25                  30

Asp Asp Leu Ala Asn Val Phe Phe Thr Arg Asn Asn Gln Val Ile Asn
            35                  40                  45

Gly Gln Asn Leu Pro Gly Leu Gly Phe Asn Ile Ala Arg Tyr Asn Ala
        50                  55                  60

Gly Ala Cys Ser Thr Asn Thr Tyr Asn Gly Ser Ser Met Val Val Ser
65                  70                  75                  80

Ser Ser Ile Lys Pro Ser Arg Gln Val Asp Gly Tyr Trp Leu Asp Trp
                85                  90                  95

Ala Ser Thr Asp Pro Ala Ser Ser Trp Asn Trp Asn Val Asp Ala
            100                 105                 110

Asn Gln Arg Ala Met Leu Gln Lys Ala Lys Ala Asn Gly Ala Asn Ile
        115                 120                 125

Phe Glu Leu Phe Ser Asn Ser Pro Met Trp Trp Met Cys Leu Asn His
130                 135                 140

Asn Pro Ser Gly Ser Gly Ser Ser Asp Asn Leu Gln Ser Trp Asn Tyr
145                 150                 155                 160

Gln Asn His Ala Val Tyr Leu Ala Asn Ile Ala Gln His Ala Gln Gln
                165                 170                 175

Asn Trp Gly Ile Gln Phe Gln Ser Val Glu Ala Phe Asn Glu Pro Ser
            180                 185                 190

Ser Gly Trp Gly Pro Thr Gly Thr Gln Glu Gly Cys His Phe Ala Val
        195                 200                 205

```
Ser Thr Met Ala Thr Val Ile Gly Tyr Leu Asn Thr Glu Leu Ala Gln
        210                 215                 220

Arg Gly Leu Ser Ser Phe Ile Ser Ala Ser Asp Glu Thr Ser Tyr Asp
225                 230                 235                 240

Leu Ala Ile Ser Thr Trp Gln Gly Leu Gly Ser Ser Ala Gln Asn Ala
                245                 250                 255

Val Lys Arg Val Asn Val His Gly Tyr Gln Gly Gly Gly Arg Arg
        260                 265                 270

Asp Thr Leu Tyr Ser Leu Val Ser Gln Ala Gly Lys Arg Leu Trp Asn
                275                 280                 285

Ser Glu Tyr Gly Asp Ala Asp Ala Ser Gly Lys Ser Met Tyr Thr Asn
        290                 295                 300

Leu Leu Leu Asp Phe Thr Trp Leu His Pro Thr Ala Trp Val Tyr Trp
305                 310                 315                 320

Gln Ala Ile Asp Gly Ser Gly Trp Gly Leu Ile Val Gly Asp Asn Asp
                325                 330                 335

Gln Leu Thr Leu Ser Ser Ala Ser Thr Lys Tyr Phe Val Leu Ala Gln
                340                 345                 350

Leu Thr Arg His Ile Arg Pro Gly Met Gln Ile Leu Thr Thr Pro Asp
        355                 360                 365

Gly Asn Thr Val Ala Ala Tyr Asp Ser Gly Ser Gln Lys Leu Val Ile
370                 375                 380

Val Ala Ala Asn Trp Gly Ser Ala Gln Thr Ile Thr Phe Asp Leu Thr
385                 390                 395                 400

Arg Ala Lys Thr Ala Gly Ser Asn Gly Ala Thr Val Pro Arg Trp Ser
                405                 410                 415

Thr Gln Thr Ser Gly Gly Asp Gln Tyr Lys Ser Tyr Ser Asp Thr Lys
                420                 425                 430

Ile Asn Asn Gly Lys Phe Ser Val Ser Phe Ser Thr Gly Gln Val Gln
                435                 440                 445

Thr Phe Glu Ile Ser Gly Val Val Leu Lys
        450                 455

<210> SEQ ID NO 20
<211> LENGTH: 463
<212> TYPE: PRT
<213> ORGANISM: Streptomyces davawensis

<400> SEQUENCE: 20

Asp Ala Thr Ile Val Ile Asn Pro Gly Thr Arg Tyr Gly Thr Trp Glu
1               5                   10                  15

Gly Trp Gly Thr Ser Leu Ala Trp Trp Gly Asn Val Phe Gly Thr Arg
                20                  25                  30

Asp Asp Phe Ala Asp Leu Phe Phe Thr Thr Lys Ser Val Thr Tyr Asn
            35                  40                  45

Gly Thr Ser Leu Pro Gly Leu Gly Leu Asn Ile Ala Arg Tyr Asn Leu
        50                  55                  60

Gly Ala Cys Ser Trp Asn Ala Val Asn Gly Glu Thr Met Val Lys Ser
65                  70                  75                  80

Pro Asn Ile Pro Ala Phe Lys Gln Ile Glu Gly Phe Trp Gln Asp Trp
                85                  90                  95

Asn Asn Glu Asp Pro Thr Ser Ser Ala Trp Asp Trp Thr Ala Asp Ala
            100                 105                 110

Thr Gln Arg Ala Met Leu Val Lys Ala Thr Gln Arg Gly Ala Val Thr
```

```
            115                 120                 125
Glu Leu Phe Ala Asn Ser Pro Met Trp Trp Met Cys Tyr Asn His Asn
130                 135                 140

Pro Ser Gly Ala Ala Asp Gly Gly Asn Asn Leu Gln Thr Trp Asn Tyr
145                 150                 155                 160

Arg Gln His Ala Ser His Leu Ala Ala Val Ala Leu Tyr Ala Arg Thr
                165                 170                 175

Asn Trp Gly Val Asn Phe Ala Thr Val Asp Pro Phe Asn Glu Pro Ala
                180                 185                 190

Ser Ser Trp Trp Thr Ala Ser Gly Thr Gln Glu Gly Cys His Leu Asp
        195                 200                 205

Pro Ala Val Gln Ala Ala Val Leu Pro Tyr Met Arg Ser Glu Leu Asp
210                 215                 220

Lys Arg Gly Leu Thr Gly Val Arg Ile Ser Ala Ser Asp Glu Thr Asn
225                 230                 235                 240

Tyr Asp Thr Ala Arg Ser Thr Trp Ser Ser Phe Gly Ser Ala Thr Lys
                245                 250                 255

Ala Leu Val Ser Gln Val Asn Val His Gly Tyr Gln Gly Thr Gly Gly
                260                 265                 270

Arg Arg Asp Leu Leu Tyr Thr Asp Val Val Thr Thr Ser Gly Lys Lys
        275                 280                 285

Leu Trp Asn Ser Glu Thr Gly Asp Ser Asp Thr Gly Leu Ser Met
290                 295                 300

Ala Arg Asn Leu Cys Tyr Asp Phe Arg Trp Leu His Pro Thr Ala Trp
305                 310                 315                 320

Cys Tyr Trp Gln Val Met Asp Pro Ser Thr Gly Trp Ala Met Ile Ala
                325                 330                 335

Tyr Asp Ala Asn Thr Leu Gln Pro Thr Val Gln Pro Lys Tyr Tyr
                340                 345                 350

Val Met Ala Gln Phe Ser Arg His Ile Arg Pro Gly Met Thr Ile Leu
        355                 360                 365

Asp Thr Gly Val Ser Phe Ala Ala Ala Tyr Asp Ala Ser Ala Arg
370                 375                 380

Arg Leu Val Leu Val Ala Val Asn Thr Ser Thr Ser Pro Gln Thr Phe
385                 390                 395                 400

Thr Phe Asp Leu Ser Arg Phe Thr Thr Val Thr Gly Gly Ser Gly Gly
                405                 410                 415

Leu Val Pro Arg Trp Asn Thr Val Thr Gly Gly Asp Met Tyr Arg
                420                 425                 430

Ala Tyr Thr Asn Thr Tyr Val Thr Gly Lys Ser Val Ser Ala Thr Phe
        435                 440                 445

Ala Ala Gly Ser Val Gln Thr Leu Gln Val Asp Gly Val Thr Thr
450                 455                 460

<210> SEQ ID NO 21
<211> LENGTH: 464
<212> TYPE: PRT
<213> ORGANISM: Streptomyces avermitilis

<400> SEQUENCE: 21

Asp Ala Thr Ile Ala Val Asn Pro Ser Thr Thr Tyr Gly Lys Trp Glu
1               5                   10                  15

Gly Trp Gly Thr Ser Leu Ala Trp Ala Asn Val Phe Gly Ala Arg
            20                  25                  30
```

-continued

```
Asp Asp Phe Ala Asp Leu Phe Phe Thr Thr Lys Ser Val Thr Tyr Asn
         35                  40                  45
Gly Arg Thr Leu Pro Gly Leu Gly Leu Asn Ile Ala Arg Tyr Asn Leu
 50                  55                  60
Gly Ala Cys Ser Trp Asn Ser Val Ser Gly Glu Ser Met Val Ala Ser
 65                  70                  75                  80
Ala Asn Ile Pro Ala Phe Lys Gln Ile Glu Gly Tyr Trp Gln Asp Trp
                 85                  90                  95
Asn Asn Glu Asp Pro Thr Ser Ser Ala Trp Lys Trp Thr Ala Asp Ala
             100                 105                 110
Ala Gln Arg Thr Met Leu Val Lys Ala Thr Ala Arg Gly Ala Thr Thr
         115                 120                 125
Glu Leu Phe Ala Asn Ser Pro Met Trp Trp Met Cys Leu Asn His Asn
130                 135                 140
Pro Ser Gly Ala Ser Gly Gly Asn Asn Leu Gln Ser Trp Asn Tyr
145                 150                 155                 160
Arg Gln His Ala Ser His Leu Ala Ala Val Ala Leu Tyr Ala Lys Ser
                 165                 170                 175
Asn Trp Gly Val Asn Phe Ala Thr Val Asp Pro Phe Asn Glu Pro Ser
             180                 185                 190
Ser Ser Trp Trp Thr Ala Thr Gly Thr Gln Glu Gly Cys His Met Asp
         195                 200                 205
Ala Ser Val Gln Ala Ala Val Leu Pro Tyr Leu Arg Ser Glu Leu Asp
210                 215                 220
Arg Arg Gly Leu Thr Gly Thr Lys Ile Ser Ala Ser Asp Glu Thr Ser
225                 230                 235                 240
Tyr Asp Leu Ala Arg Thr Thr Trp Gly Ser Phe Gly Ser Ser Thr Lys
                 245                 250                 255
Ala Leu Val Asn Arg Val Asn Val His Gly Tyr Gln Gly Ser Gly Gly
             260                 265                 270
Arg Arg Asp Leu Leu Tyr Thr Asp Val Val Thr Thr Ala Gly Lys Ala
         275                 280                 285
Leu Trp Asn Ser Glu Thr Gly Asp Ser Asp Gly Thr Gly Leu Thr Leu
290                 295                 300
Ala Ser Asn Leu Cys Leu Asp Phe Arg Trp Leu His Pro Thr Ala Trp
305                 310                 315                 320
Val Tyr Trp Gln Val Met Asp Pro Ser Ser Gly Trp Ala Met Ile Ala
                 325                 330                 335
Tyr Asp Ala Ser Thr Leu Gln Pro Gly Ala Val Gln Thr Lys Tyr Tyr
             340                 345                 350
Val Met Ala Gln Phe Ser Arg His Ile Arg Ala Gly Met Thr Ile Val
         355                 360                 365
Asp Thr Gly Val Gly Tyr Ala Ala Ala Tyr Asp Ala Thr Ala Arg
370                 375                 380
Arg Leu Val Ile Val Ala Val Asn Thr Ser Thr Ser Ala Gln Thr Leu
385                 390                 395                 400
Thr Phe Asp Leu Ser Arg Phe Ser Thr Val Thr Gly Thr Gly Gly
                 405                 410                 415
Leu Val Arg Arg Trp Asn Thr Val Thr Gly Gly Gly Asp Leu Tyr
             420                 425                 430
Ala Ala His Ser Asp Thr Tyr Leu Ser Gly Lys Ser Leu Ser Val Pro
         435                 440                 445
Phe Ala Ala Gly Ala Val Gln Thr Leu Glu Val Asp Gly Val Thr Val
```

<210> SEQ ID NO 22
<211> LENGTH: 458
<212> TYPE: PRT
<213> ORGANISM: Trichoderma harzianum

<400> SEQUENCE: 22

```
Asp Thr Thr Leu Ser Ile Asp Pro Thr Ser Asn Trp Gly Thr Trp Glu
1               5                   10                  15

Gly Trp Gly Val Ser Leu Ala Trp Trp Ala Lys Ala Phe Gly Asn Arg
            20                  25                  30

Asp Asp Leu Ala Asn Val Phe Phe Thr Arg Asn Asn Gln Val Ile Asn
        35                  40                  45

Gly Gln Asn Leu Pro Gly Leu Gly Phe Asn Ile Ala Arg Tyr Asn Ala
    50                  55                  60

Gly Ala Cys Ser Thr Asn Thr Tyr Asn Gly Ser Ser Met Val Val Ser
65                  70                  75                  80

Ser Ser Ile Lys Pro Ser Arg Gln Val Asp Gly Tyr Trp Leu Asp Trp
                85                  90                  95

Ala Ser Thr Asp Pro Ala Ser Ser Trp Asn Trp Asn Val Asp Ala
            100                 105                 110

Asn Gln Arg Ala Met Leu Gln Lys Ala Lys Ala Asn Gly Ala Asn Ile
        115                 120                 125

Phe Glu Leu Phe Ser Asn Ser Pro Met Trp Trp Met Cys Leu Asn His
130                 135                 140

Asn Pro Ser Gly Ser Gly Ser Ser Asp Asn Leu Gln Ser Trp Asn Tyr
145                 150                 155                 160

Gln Asn His Ala Val Tyr Leu Ala Asn Ile Ala Gln His Ala Gln Gln
                165                 170                 175

Asn Trp Gly Ile Gln Phe Gln Ser Val Glu Ala Phe Asn Glu Pro Ser
            180                 185                 190

Ser Gly Trp Gly Pro Thr Gly Thr Gln Glu Gly Cys His Phe Ala Val
        195                 200                 205

Ser Thr Met Ala Thr Val Ile Gly Tyr Leu Asn Thr Glu Leu Ala Gln
    210                 215                 220

Arg Gly Leu Ser Ser Phe Ile Ser Ala Ser Asp Glu Thr Ser Tyr Asp
225                 230                 235                 240

Leu Ala Ile Ser Thr Trp Gln Gly Leu Gly Ser Ser Ala Gln Asn Ala
                245                 250                 255

Val Lys Arg Val Asn Val His Gly Tyr Gln Gly Gly Gly Arg Arg
            260                 265                 270

Asp Thr Leu Tyr Ser Leu Val Ser Gln Ala Gly Lys Arg Leu Trp Asn
        275                 280                 285

Ser Glu Tyr Gly Asp Ala Asp Ala Ser Gly Lys Ser Met Tyr Thr Asn
    290                 295                 300

Leu Leu Leu Asp Phe Thr Trp Leu His Pro Thr Ala Trp Val Tyr Trp
305                 310                 315                 320

Gln Ala Ile Asp Gly Ser Gly Trp Gly Leu Ile Val Gly Asp Asn Asp
                325                 330                 335

Gln Leu Thr Leu Ser Ser Ala Ser Thr Lys Tyr Phe Val Leu Ala Gln
            340                 345                 350

Leu Thr Arg His Ile Arg Pro Gly Met Gln Ile Leu Thr Thr Pro Asp
        355                 360                 365
```

```
Gly Asn Thr Val Ala Ala Tyr Asp Ser Gly Ser Gln Lys Leu Val Ile
    370                 375                 380

Val Ala Ala Asn Trp Gly Ser Ala Gln Thr Ile Thr Phe Asp Leu Thr
385                 390                 395                 400

Arg Ala Lys Thr Ala Gly Ser Asn Gly Ala Thr Val Pro Arg Trp Ser
                405                 410                 415

Thr Gln Thr Ser Gly Gly Asp Gln Tyr Lys Ser Tyr Ser Asp Thr Lys
            420                 425                 430

Ile Asn Asn Gly Lys Phe Ser Val Ser Phe Ser Thr Gly Gln Val Gln
        435                 440                 445

Thr Phe Glu Ile Ser Gly Val Val Leu Lys
    450                 455

<210> SEQ ID NO 23
<211> LENGTH: 463
<212> TYPE: PRT
<213> ORGANISM: Streptomyces davawensis

<400> SEQUENCE: 23

Asp Ala Thr Ile Val Ile Asn Pro Gly Thr Arg Tyr Gly Thr Trp Glu
1               5                   10                  15

Gly Trp Gly Thr Ser Leu Ala Trp Trp Gly Asn Val Phe Gly Thr Arg
            20                  25                  30

Asp Asp Phe Ala Asp Leu Phe Phe Thr Thr Lys Ser Val Thr Tyr Asn
        35                  40                  45

Gly Thr Ser Leu Pro Gly Leu Gly Leu Asn Ile Ala Arg Tyr Asn Leu
    50                  55                  60

Gly Ala Cys Ser Trp Asn Ala Val Asn Gly Glu Thr Met Val Lys Ser
65                  70                  75                  80

Pro Asn Ile Pro Ala Phe Lys Gln Ile Glu Gly Phe Trp Gln Asp Trp
                85                  90                  95

Asn Asn Glu Asp Pro Thr Ser Ser Ala Trp Asp Trp Thr Ala Asp Ala
            100                 105                 110

Thr Gln Arg Ala Met Leu Val Lys Ala Thr Gln Arg Gly Ala Val Thr
        115                 120                 125

Glu Leu Phe Ala Asn Ser Pro Met Trp Trp Met Cys Tyr Asn His Asn
    130                 135                 140

Pro Ser Gly Ala Ala Asp Gly Gly Asn Asn Leu Gln Thr Trp Asn Tyr
145                 150                 155                 160

Arg Gln His Ala Ser His Leu Ala Ala Val Ala Leu Tyr Ala Arg Thr
                165                 170                 175

Asn Trp Gly Val Asn Phe Ala Thr Val Asp Pro Phe Asn Glu Pro Ala
            180                 185                 190

Ser Ser Trp Trp Thr Ala Ser Gly Thr Gln Glu Gly Cys His Leu Asp
        195                 200                 205

Pro Ala Val Gln Ala Ala Val Leu Pro Tyr Met Arg Ser Glu Leu Asp
    210                 215                 220

Lys Arg Gly Leu Thr Gly Val Arg Ile Ser Ala Ser Asp Glu Thr Asn
225                 230                 235                 240

Tyr Asp Thr Ala Arg Ser Thr Trp Ser Ser Phe Gly Ser Ala Thr Lys
                245                 250                 255

Ala Leu Val Ser Gln Val Asn Val His Gly Tyr Gln Gly Thr Gly Gly
            260                 265                 270

Arg Arg Asp Leu Leu Tyr Thr Asp Val Val Thr Thr Ser Gly Lys Lys
        275                 280                 285
```

Leu Trp Asn Ser Glu Thr Gly Asp Ser Asp Gly Thr Gly Leu Ser Met
            290                 295                 300

Ala Arg Asn Leu Cys Tyr Asp Phe Arg Trp Leu His Pro Thr Ala Trp
305                 310                 315                 320

Cys Tyr Trp Gln Val Met Asp Pro Ser Thr Gly Trp Ala Met Ile Ala
                    325                 330                 335

Tyr Asp Ala Asn Thr Leu Gln Pro Thr Thr Val Gln Pro Lys Tyr Tyr
                340                 345                 350

Val Met Ala Gln Phe Ser Arg His Ile Arg Pro Gly Met Thr Ile Leu
            355                 360                 365

Asp Thr Gly Val Ser Phe Ala Ala Ala Tyr Asp Ala Ser Ala Arg
370                 375                 380

Arg Leu Val Leu Val Ala Val Asn Thr Ser Thr Ser Pro Gln Thr Phe
385                 390                 395                 400

Thr Phe Asp Leu Ser Arg Phe Thr Thr Val Thr Gly Ser Gly Gly
                    405                 410                 415

Leu Val Pro Arg Trp Asn Thr Val Thr Gly Gly Asp Met Tyr Arg
                420                 425                 430

Ala Tyr Thr Asn Thr Tyr Val Thr Gly Lys Ser Val Ser Ala Thr Phe
            435                 440                 445

Ala Ala Gly Ser Val Gln Thr Leu Gln Val Asp Gly Val Thr Thr
    450                 455                 460

<210> SEQ ID NO 24
<211> LENGTH: 464
<212> TYPE: PRT
<213> ORGANISM: Streptomyces avermitilis

<400> SEQUENCE: 24

Asp Ala Thr Ile Ala Val Asn Pro Ser Thr Thr Tyr Gly Lys Trp Glu
1               5                   10                  15

Gly Trp Gly Thr Ser Leu Ala Trp Trp Ala Asn Val Phe Gly Ala Arg
                20                  25                  30

Asp Asp Phe Ala Asp Leu Phe Phe Thr Thr Lys Ser Val Thr Tyr Asn
            35                  40                  45

Gly Arg Thr Leu Pro Gly Leu Gly Leu Asn Ile Ala Arg Tyr Asn Leu
        50                  55                  60

Gly Ala Cys Ser Trp Asn Ser Val Ser Gly Glu Ser Met Val Ala Ser
65                  70                  75                  80

Ala Asn Ile Pro Ala Phe Lys Gln Ile Glu Gly Tyr Trp Gln Asp Trp
                85                  90                  95

Asn Asn Glu Asp Pro Thr Ser Ser Ala Trp Lys Trp Thr Ala Asp Ala
            100                 105                 110

Ala Gln Arg Thr Met Leu Val Lys Ala Thr Arg Gly Ala Thr Thr
        115                 120                 125

Glu Leu Phe Ala Asn Ser Pro Met Trp Trp Met Cys Leu Asn His Asn
    130                 135                 140

Pro Ser Gly Ala Ser Gly Gly Asn Asn Leu Gln Ser Trp Asn Tyr
145                 150                 155                 160

Arg Gln His Ala Ser His Leu Ala Ala Val Ala Leu Tyr Ala Lys Ser
                165                 170                 175

Asn Trp Gly Val Asn Phe Ala Thr Val Asp Pro Phe Asn Glu Pro Ser
            180                 185                 190

Ser Ser Trp Trp Thr Ala Thr Gly Thr Gln Glu Gly Cys His Met Asp

```
            195                 200                 205
Ala Ser Val Gln Ala Val Leu Pro Tyr Leu Arg Ser Glu Leu Asp
210                 215                 220

Arg Arg Gly Leu Thr Gly Thr Lys Ile Ser Ala Ser Asp Glu Thr Ser
225                 230                 235                 240

Tyr Asp Leu Ala Arg Thr Thr Trp Gly Ser Phe Gly Ser Ser Thr Lys
                    245                 250                 255

Ala Leu Val Asn Arg Val Asn Val His Gly Tyr Gln Gly Ser Gly Gly
                260                 265                 270

Arg Arg Asp Leu Leu Tyr Thr Asp Val Val Thr Thr Ala Gly Lys Ala
275                 280                 285

Leu Trp Asn Ser Glu Thr Gly Asp Ser Asp Gly Thr Gly Leu Thr Leu
290                 295                 300

Ala Ser Asn Leu Cys Leu Asp Phe Arg Trp Leu His Pro Thr Ala Trp
305                 310                 315                 320

Val Tyr Trp Gln Val Met Asp Pro Ser Ser Gly Trp Ala Met Ile Ala
                    325                 330                 335

Tyr Asp Ala Ser Thr Leu Gln Pro Gly Ala Val Gln Thr Lys Tyr Tyr
                340                 345                 350

Val Met Ala Gln Phe Ser Arg His Ile Arg Ala Gly Met Thr Ile Val
                355                 360                 365

Asp Thr Gly Val Gly Tyr Ala Ala Ala Tyr Asp Ala Thr Ala Arg
370                 375                 380

Arg Leu Val Ile Val Ala Val Asn Thr Ser Thr Ser Ala Gln Thr Leu
385                 390                 395                 400

Thr Phe Asp Leu Ser Arg Phe Ser Thr Val Thr Gly Thr Gly Gly
                    405                 410                 415

Leu Val Arg Arg Trp Asn Thr Val Thr Gly Gly Gly Asp Leu Tyr
                420                 425                 430

Ala Ala His Ser Asp Thr Tyr Leu Ser Gly Lys Ser Leu Ser Val Pro
                435                 440                 445

Phe Ala Ala Gly Ala Val Gln Thr Leu Glu Val Asp Gly Val Thr Val
450                 455                 460

<210> SEQ ID NO 25
<211> LENGTH: 458
<212> TYPE: PRT
<213> ORGANISM: Trichoderma harzianum

<400> SEQUENCE: 25

Asp Thr Thr Leu Ser Ile Asp Pro Thr Ser Asn Trp Gly Thr Trp Glu
1               5                   10                  15

Gly Trp Gly Val Ser Leu Ala Trp Ala Lys Ala Phe Gly Asn Arg
                20                  25                  30

Asp Asp Leu Ala Asn Val Phe Phe Thr Arg Asn Asn Gln Val Ile Asn
            35                  40                  45

Gly Gln Asn Leu Pro Gly Leu Gly Phe Asn Ile Ala Arg Tyr Asn Ala
        50                  55                  60

Gly Ala Cys Ser Thr Asn Thr Tyr Asn Gly Ser Ser Met Val Val Ser
65                  70                  75                  80

Ser Ser Ile Lys Pro Ser Arg Gln Val Asp Gly Tyr Trp Leu Asp Trp
                85                  90                  95

Ala Ser Thr Asp Pro Ala Ser Ser Trp Asn Trp Asn Val Asp Ala
            100                 105                 110
```

Asn Gln Arg Ala Met Leu Gln Lys Ala Lys Ala Asn Gly Ala Asn Ile
115                 120                 125

Phe Glu Leu Phe Ser Asn Ser Pro Met Trp Trp Met Cys Leu Asn His
130                 135                 140

Asn Pro Ser Gly Ser Gly Ser Ser Asp Asn Leu Gln Ser Trp Asn Tyr
145                 150                 155                 160

Gln Asn His Ala Val Tyr Leu Ala Asn Ile Ala Gln His Ala Gln Gln
                165                 170                 175

Asn Trp Gly Ile Gln Phe Gln Ser Val Glu Ala Phe Asn Glu Pro Ser
                180                 185                 190

Ser Gly Trp Gly Pro Thr Gly Thr Gln Glu Gly Cys His Phe Ala Val
                195                 200                 205

Ser Thr Met Ala Thr Val Ile Gly Tyr Leu Asn Thr Glu Leu Ala Gln
        210                 215                 220

Arg Gly Leu Ser Ser Phe Ile Ser Ala Ser Asp Glu Thr Ser Tyr Asp
225                 230                 235                 240

Leu Ala Ile Ser Thr Trp Gln Gly Leu Gly Ser Ser Ala Gln Asn Ala
                245                 250                 255

Val Lys Arg Val Asn Val His Gly Tyr Gln Gly Gly Gly Arg Arg
                260                 265                 270

Asp Thr Leu Tyr Ser Leu Val Ser Gln Ala Gly Lys Arg Leu Trp Asn
        275                 280                 285

Ser Glu Tyr Gly Asp Ala Asp Ala Ser Gly Lys Ser Met Tyr Thr Asn
        290                 295                 300

Leu Leu Leu Asp Phe Thr Trp Leu His Pro Thr Ala Trp Val Tyr Trp
305                 310                 315                 320

Gln Ala Ile Asp Gly Ser Gly Trp Gly Leu Ile Val Gly Asp Asn Asp
                325                 330                 335

Gln Leu Thr Leu Ser Ser Ala Ser Thr Lys Tyr Phe Val Leu Ala Gln
                340                 345                 350

Leu Thr Arg His Ile Arg Pro Gly Met Gln Ile Leu Thr Thr Pro Asp
                355                 360                 365

Gly Asn Thr Val Ala Ala Tyr Asp Ser Gly Ser Gln Lys Leu Val Ile
        370                 375                 380

Val Ala Ala Asn Trp Gly Ser Ala Gln Thr Ile Thr Phe Asp Leu Thr
385                 390                 395                 400

Arg Ala Lys Thr Ala Gly Ser Asn Gly Ala Thr Val Pro Arg Trp Ser
                405                 410                 415

Thr Gln Thr Ser Gly Gly Asp Gln Tyr Lys Ser Tyr Ser Asp Thr Lys
                420                 425                 430

Ile Asn Asn Gly Lys Phe Ser Val Ser Phe Ser Thr Gly Gln Val Gln
                435                 440                 445

Thr Phe Glu Ile Ser Gly Val Val Leu Lys
        450                 455

<210> SEQ ID NO 26
<211> LENGTH: 541
<212> TYPE: PRT
<213> ORGANISM: Ascobolus stictoideus

<400> SEQUENCE: 26

Gln Thr Tyr Thr Leu Glu Ala Glu Ala Gly Thr Leu Thr Gly Val Thr
1               5                   10                  15

Val Met Asn Glu Ile Ala Gly Phe Ser Gly Thr Gly Tyr Val Gly Gly
                20                  25                  30

-continued

Trp Asp Glu Asp Ala Asp Thr Val Ser Leu Thr Phe Thr Ser Asp Ala
    35                  40                  45

Thr Lys Leu Tyr Asp Val Lys Ile Arg Tyr Ser Gly Pro Tyr Gly Ser
    50                  55                  60

Lys Tyr Thr Arg Ile Ser Tyr Asn Gly Ala Thr Gly Gly Asp Ile Ser
65                  70                  75                  80

Leu Pro Glu Thr Thr Glu Trp Ala Thr Val Asn Ala Gly Gln Ala Leu
                85                  90                  95

Leu Asn Ala Gly Ser Asn Thr Ile Lys Leu His Asn Asn Trp Gly Trp
                100                 105                 110

Tyr Leu Ile Asp Ala Val Ile Leu Thr Pro Ser Val Pro Arg Pro Pro
            115                 120                 125

His Gln Val Thr Asp Ala Leu Val Asn Thr Asn Ser Asn Ala Val Thr
        130                 135                 140

Lys Gln Leu Met Lys Phe Leu Val Ser Lys Tyr His Lys Ala Tyr Ile
145                 150                 155                 160

Thr Gly Gln Gln Glu Leu His Ala His Gln Trp Val Glu Lys Asn Val
                165                 170                 175

Gly Lys Ser Pro Ala Ile Leu Gly Leu Asp Phe Met Asp Tyr Ser Pro
                180                 185                 190

Ser Arg Val Glu Phe Gly Thr Thr Ser Gln Ala Val Glu Gln Ala Ile
            195                 200                 205

Asp Phe Asp Lys Arg Gly Gly Ile Val Thr Phe Ala Trp His Trp Asn
        210                 215                 220

Ala Pro Ser Gly Leu Ile Asn Thr Pro Gly Ser Glu Trp Trp Arg Gly
225                 230                 235                 240

Phe Tyr Thr Glu His Thr Thr Phe Asp Val Ala Ala Ala Leu Gln Asn
                245                 250                 255

Thr Thr Asn Ala Asn Tyr Asn Leu Leu Ile Arg Asp Ile Asp Ala Ile
                260                 265                 270

Ala Val Gln Leu Lys Arg Leu Gln Thr Ala Gly Val Pro Val Leu Trp
            275                 280                 285

Arg Pro Leu His Glu Ala Glu Gly Gly Trp Phe Trp Trp Gly Ala Lys
        290                 295                 300

Gly Pro Glu Pro Ala Lys Lys Leu Tyr Lys Ile Leu Tyr Asp Arg Leu
305                 310                 315                 320

Thr Asn Tyr His Lys Leu Asn Asn Leu Ile Trp Val Trp Asn Ser Val
                325                 330                 335

Ala Lys Asp Trp Tyr Pro Gly Asp Glu Ile Val Asp Val Leu Ser Phe
            340                 345                 350

Asp Ser Tyr Pro Ala Gln Pro Gly Asp His Gly Pro Val Ser Ala Gln
        355                 360                 365

Tyr Asn Ala Leu Val Glu Leu Gly Lys Asp Lys Lys Leu Ile Ala Ala
    370                 375                 380

Thr Glu Val Gly Thr Ile Pro Asp Pro Asp Leu Met Gln Leu Tyr Glu
385                 390                 395                 400

Ser Tyr Trp Ser Phe Phe Val Thr Trp Glu Gly Glu Phe Ile Glu Asn
                405                 410                 415

Gly Val His Asn Ser Leu Glu Phe Leu Lys Lys Leu Tyr Asn Asn Ser
                420                 425                 430

Phe Val Leu Asn Leu Asp Thr Ile Gln Gly Trp Lys Asn Gly Ala Gly
            435                 440                 445

```
Ser Ser Thr Thr Thr Val Lys Ser Thr Thr Thr Pro Thr Thr Thr
450                 455                 460

Ile Lys Ser Thr Thr Thr Pro Val Thr Thr Pro Thr Thr Val Lys
465                 470                 475                 480

Thr Thr Thr Thr Pro Thr Thr Ala Thr Val Lys Ser Thr Thr
            485                 490                 495

Thr Thr Ala Gly Pro Thr Pro Thr Ala Val Ala Gly Arg Trp Gln Gln
            500                 505                 510

Cys Gly Gly Ile Gly Phe Thr Gly Pro Thr Thr Cys Glu Ala Gly Thr
            515                 520                 525

Thr Cys Asn Val Leu Asn Pro Tyr Tyr Ser Gln Cys Leu
            530                 535                 540

<210> SEQ ID NO 27
<211> LENGTH: 541
<212> TYPE: PRT
<213> ORGANISM: Ascobolus stictoideus

<400> SEQUENCE: 27

Gln Thr Tyr Thr Leu Glu Ala Glu Ala Gly Thr Leu Thr Gly Val Thr
1               5                   10                  15

Val Met Asn Glu Ile Ala Gly Phe Ser Gly Thr Gly Tyr Val Gly Gly
                20                  25                  30

Trp Asp Glu Asp Ala Asp Thr Val Ser Leu Thr Phe Thr Ser Asp Ala
            35                  40                  45

Thr Lys Leu Tyr Asp Val Lys Ile Arg Tyr Ser Gly Pro Tyr Gly Ser
50                  55                  60

Lys Tyr Thr Arg Ile Ser Tyr Asn Gly Ala Thr Gly Gly Asp Ile Ser
65                  70                  75                  80

Leu Pro Glu Thr Thr Glu Trp Ala Thr Val Asn Ala Gly Gln Ala Leu
                85                  90                  95

Leu Asn Ala Gly Ser Asn Thr Ile Lys Leu His Asn Asn Trp Gly Trp
            100                 105                 110

Tyr Leu Ile Asp Ala Val Ile Leu Thr Pro Ser Val Pro Arg Pro Pro
        115                 120                 125

His Gln Val Thr Asp Ala Leu Val Asn Thr Asn Ser Asn Ala Val Thr
130                 135                 140

Lys Gln Leu Met Lys Phe Leu Val Ser Lys Tyr His Lys Ala Tyr Ile
145                 150                 155                 160

Thr Gly Gln Gln Glu Leu His Ala His Gln Trp Val Glu Lys Asn Val
                165                 170                 175

Gly Lys Ser Pro Ala Ile Leu Gly Leu Asp Phe Met Asp Tyr Ser Pro
            180                 185                 190

Ser Arg Val Glu Phe Gly Thr Thr Ser Gln Ala Val Glu Gln Ala Ile
        195                 200                 205

Asp Phe Asp Lys Arg Gly Gly Ile Val Thr Phe Ala Trp His Trp Asn
210                 215                 220

Ala Pro Ser Gly Leu Ile Asn Thr Pro Gly Ser Glu Trp Trp Arg Gly
225                 230                 235                 240

Phe Tyr Thr Glu His Thr Thr Phe Asp Val Ala Ala Leu Gln Asn
                245                 250                 255

Thr Thr Asn Ala Asn Tyr Asn Leu Leu Ile Arg Asp Ile Asp Ala Ile
            260                 265                 270

Ala Val Gln Leu Lys Arg Leu Gln Thr Ala Gly Val Pro Val Leu Trp
        275                 280                 285
```

Arg Pro Leu His Glu Ala Glu Gly Gly Trp Phe Trp Trp Gly Ala Lys
            290                 295                 300

Gly Pro Glu Pro Ala Lys Lys Leu Tyr Lys Ile Leu Tyr Asp Arg Leu
305                 310                 315                 320

Thr Asn Tyr His Lys Leu Asn Asn Leu Ile Trp Val Trp Asn Ser Val
            325                 330                 335

Ala Lys Asp Trp Tyr Pro Gly Asp Glu Ile Val Asp Val Leu Ser Phe
            340                 345                 350

Asp Ser Tyr Pro Ala Gln Pro Gly Asp His Gly Pro Val Ser Ala Gln
            355                 360                 365

Tyr Asn Ala Leu Val Glu Leu Gly Lys Asp Lys Leu Ile Ala Ala
            370                 375                 380

Thr Glu Val Gly Thr Ile Pro Asp Pro Asp Leu Met Gln Leu Tyr Glu
385                 390                 395                 400

Ser Tyr Trp Ser Phe Phe Val Thr Trp Glu Gly Glu Phe Ile Glu Asn
            405                 410                 415

Gly Val His Asn Ser Leu Glu Phe Leu Lys Lys Leu Tyr Asn Asn Ser
            420                 425                 430

Phe Val Leu Asn Leu Asp Thr Ile Gln Gly Trp Lys Asn Gly Ala Gly
            435                 440                 445

Ser Ser Thr Thr Thr Val Lys Ser Thr Thr Thr Pro Thr Thr Thr
450                 455                 460

Ile Lys Ser Thr Thr Thr Pro Val Thr Thr Pro Thr Thr Val Lys
465                 470                 475                 480

Thr Thr Thr Thr Pro Thr Thr Thr Ala Thr Val Lys Ser Thr Thr
                    485                 490                 495

Thr Thr Ala Gly Pro Thr Pro Thr Ala Val Ala Gly Arg Trp Gln Gln
            500                 505                 510

Cys Gly Gly Ile Gly Phe Thr Gly Pro Thr Cys Glu Ala Gly Thr
            515                 520                 525

Thr Cys Asn Val Leu Asn Pro Tyr Tyr Ser Gln Cys Leu
            530                 535                 540

<210> SEQ ID NO 28
<211> LENGTH: 526
<212> TYPE: PRT
<213> ORGANISM: Chaetomium virescens

<400> SEQUENCE: 28

Pro Arg Asp Pro Gly Ala Thr Ala Arg Thr Phe Glu Ala Glu Asp Ala
1               5                   10                  15

Thr Leu Ala Gly Thr Asn Val Asp Thr Ala Leu Ser Gly Phe Thr Gly
            20                  25                  30

Thr Gly Tyr Val Thr Gly Phe Asp Gln Ala Ala Asp Lys Val Thr Phe
        35                  40                  45

Thr Val Asp Ser Ala Ser Thr Glu Leu Tyr Asp Leu Ser Ile Arg Val
    50                  55                  60

Ala Ala Ile Tyr Gly Asp Lys Arg Thr Ser Val Val Leu Asn Gly Gly
65                  70                  75                  80

Ala Ser Ser Glu Val Tyr Phe Pro Ala Gly Glu Thr Trp Thr Asn Val
                85                  90                  95

Ala Ala Gly Gln Leu Leu Leu Asn Gln Gly Ser Asn Thr Ile Asp Ile
            100                 105                 110

Val Ser Asn Trp Gly Trp Tyr Leu Ile Asp Ser Ile Thr Leu Thr Pro

```
            115                 120                 125
Ser Thr Pro Arg Pro Ala His Gln Ile Asn Glu Ala Pro Val Asn Ala
130                 135                 140

Ala Ala Asp Lys Asn Ala Lys Ala Leu Tyr Ser Tyr Leu Arg Ser Ile
145                 150                 155                 160

Tyr Gly Lys Lys Ile Leu Ser Gly Gln Gln Glu Leu Ser Leu Ser Asn
                165                 170                 175

Trp Ile Ala Gln Gln Thr Gly Lys Thr Pro Ala Leu Val Ser Val Asp
                180                 185                 190

Leu Met Asp Tyr Ser Pro Ser Arg Val Glu Arg Gly Thr Val Gly Thr
                195                 200                 205

Ala Val Glu Glu Ala Ile Gln His His Asn Arg Gly Gly Ile Val Ser
210                 215                 220

Val Leu Trp His Trp Asn Ala Pro Thr Gly Leu Tyr Asp Thr Glu Glu
225                 230                 235                 240

His Arg Trp Trp Ser Gly Phe Tyr Thr Ser Ala Thr Asp Phe Asp Val
                245                 250                 255

Ala Ala Ala Leu Ser Ser Thr Thr Asn Ala Asn Tyr Thr Leu Leu Ile
                260                 265                 270

Arg Asp Ile Asp Ala Ile Ala Val Gln Leu Lys Arg Leu Gln Ser Ala
                275                 280                 285

Gly Val Pro Val Leu Phe Arg Pro Leu His Glu Ala Glu Gly Gly Trp
290                 295                 300

Phe Trp Trp Gly Ala Lys Gly Pro Glu Pro Ala Lys Lys Leu Trp Gly
305                 310                 315                 320

Ile Leu Tyr Asp Arg Val Thr Asn His His Gln Ile Asn Asn Leu Leu
                325                 330                 335

Trp Val Trp Asn Ser Ile Leu Pro Glu Trp Tyr Pro Gly Asp Ala Thr
                340                 345                 350

Val Asp Ile Leu Ser Ala Asp Val Tyr Ala Gln Gly Asn Gly Pro Met
                355                 360                 365

Ser Thr Gln Tyr Asn Gln Leu Ile Glu Leu Gly Lys Asp Lys Lys Met
370                 375                 380

Ile Ala Ala Glu Val Gly Ala Ala Pro Leu Pro Asp Leu Leu Gln
385                 390                 395                 400

Ala Tyr Glu Ala His Trp Leu Trp Phe Thr Val Trp Gly Asp Ser Phe
                405                 410                 415

Ile Asn Asn Ala Asp Trp Asn Ser Leu Asp Thr Leu Lys Lys Val Tyr
                420                 425                 430

Thr Ser Asp Tyr Val Leu Thr Leu Asp Glu Ile Gln Gly Trp Gln Gly
                435                 440                 445

Ser Thr Pro Ser Ala Thr Thr Thr Ser Ser Thr Thr Pro Ser Ala
                450                 455                 460

Thr Thr Thr Thr Thr Thr Pro Ser Thr Ala Thr Ala Thr Pro
465                 470                 475                 480

Ser Ala Thr Thr Thr Ala Ser Pro Val Thr Tyr Ala Glu His Trp Gly
                485                 490                 495

Gln Cys Ala Gly Lys Gly Trp Thr Gly Pro Thr Thr Cys Arg Pro Pro
                500                 505                 510

Tyr Thr Cys Lys Tyr Gln Asn Asp Trp Tyr Ser Gln Cys Leu
                515                 520                 525

<210> SEQ ID NO 29
```

```
<211> LENGTH: 452
<212> TYPE: PRT
<213> ORGANISM: Preussia aemulans

<400> SEQUENCE: 29

Gln Thr Val Ile Tyr Gln Ala Glu Gln Ala Lys Leu Ser Gly Val Thr
1               5                   10                  15

Val Glu Phe Ser Ile Ile Lys Gln Val Val Gly Thr Gly Tyr Val Glu
            20                  25                  30

Gly Phe Asp Glu Ser Thr Asp Ser Ile Thr Phe Thr Val Glu Ser Thr
        35                  40                  45

Thr Ala Ala Leu Tyr Asp Leu Ala Leu Thr Tyr Asn Gly Pro Tyr Gly
    50                  55                  60

Asp Lys Tyr Thr Asn Val Val Leu Asn Asn Ala Ala Gly Ser Gln Val
65                  70                  75                  80

Ser Leu Pro Ala Thr Thr Ala Trp Thr Thr Val Pro Ala Gly Gln Val
                85                  90                  95

Leu Leu Asn Ala Gly Ala Asn Thr Ile Gln Ile Gln Asn Asn Trp Gly
            100                 105                 110

Trp Tyr Leu Val Asp Ser Ile Ser Leu Lys Pro Ala Ala Thr Arg Gly
        115                 120                 125

Ala His Gln Ile Thr Thr Lys Pro Val Asn Lys Asn Ala Asn Ser Asp
    130                 135                 140

Ala Lys Ala Leu Leu Lys Tyr Leu Gly Ser Ile Tyr Gly Lys Lys Ile
145                 150                 155                 160

Leu Ser Gly Gln Gln Asp Leu Ser Ser Leu Asp Trp Val Thr Lys Asn
                165                 170                 175

Val Gly Lys Thr Pro Ala Val Leu Gly Leu Asp Thr Met Asp Tyr Ser
            180                 185                 190

Glu Ser Arg Lys Ser Arg Gly Ala Val Ser Thr Asp Val Asp Lys Ala
        195                 200                 205

Ile Ala Phe Ala Lys Lys Gly Gly Ile Val Thr Phe Cys Trp His Trp
    210                 215                 220

Gly Ala Pro Thr Gly Leu Phe Asp Ser Ala Ala Gln Pro Trp Tyr Arg
225                 230                 235                 240

Gly Phe Tyr Thr Asp Ala Thr Asp Phe Asn Ile Glu Thr Ala Leu Lys
                245                 250                 255

Asp Thr Thr Asn Ala Asn Tyr Thr Leu Leu Met Lys Asp Ile Asp Thr
            260                 265                 270

Ile Ala Val Gln Leu Lys Lys Leu Gln Asp Ala Gly Val Pro Val Ile
        275                 280                 285

Trp Arg Pro Leu His Glu Ala Glu Gly Gly Trp Phe Trp Trp Gly Ala
    290                 295                 300

Lys Gly Pro Glu Pro Ala Lys Lys Leu Trp Lys Ile Met Tyr Asp Arg
305                 310                 315                 320

Leu Thr Asn Gln His Gly Leu Asn Asn Leu Val Trp Thr Trp Asn Ser
                325                 330                 335

Val Ala Pro Asn Trp Tyr Pro Gly Asp Asp Thr Val Asp Ile Val Ser
            340                 345                 350

Ala Asp Thr Tyr Ser Gln Gly Asp His Gly Pro Ile Ser Ala Thr Tyr
        355                 360                 365

Asn Asn Leu Leu Ala Leu Thr Asn Asp Thr Lys Ile Ile Ala Ala Ala
    370                 375                 380

Glu Ile Gly Ser Val Met Glu Pro Ala Gln Leu Gln Ala Tyr Gln Ala
```

385                 390                 395                 400
Asp Trp Val Tyr Phe Cys Val Trp Ser Gly Glu Phe Ile Asp Gly Gly
                405                 410                 415

Val Trp Asn Ser Leu Asp Phe Leu Lys Lys Val Tyr Asn Asp Pro Tyr
                420                 425                 430

Val Leu Thr Leu Asp Glu Ile Gln Gly Trp Lys Thr Ala Arg Gly Lys
                435                 440                 445

Pro Arg Val Ser
    450

<210> SEQ ID NO 30
<211> LENGTH: 312
<212> TYPE: PRT
<213> ORGANISM: Yunnania penicillata

<400> SEQUENCE: 30

Ala Pro Ser Thr Thr Pro Val Asn Glu Lys Ala Thr Asp Ala Ala Lys
1               5                   10                  15

Asn Leu Leu Ser Tyr Leu Val Glu Gln Ala Ala Asn Gly Val Thr Leu
                20                  25                  30

Ser Gly Gln Gln Asp Leu Glu Ser Ala Gln Trp Val Ser Asp Asn Val
            35                  40                  45

Gly Lys Trp Pro Ala Ile Leu Gly Ile Asp Phe Met Asp Tyr Ser Pro
        50                  55                  60

Ser Arg Val Glu Tyr Gly Ala Val Gly Ser Thr Val Pro Asp Ala Ile
65                  70                  75                  80

Ser Tyr Asp Ser Asp Gly Gly Ile Val Thr Phe Cys Trp His Trp Gly
                85                  90                  95

Ser Pro Ser Gly Thr Tyr Asn Thr Thr Asp Gln Pro Trp Trp Ser Asn
                100                 105                 110

Phe Tyr Thr Glu Ala Thr Ala Phe Asp Ile Ala Ala Met Asp Asp
            115                 120                 125

Pro Asp Ser Ala Asp Tyr Asn Leu Leu Val Arg Asp Ile Asp Ala Ile
        130                 135                 140

Ser Glu Leu Leu Leu Gln Leu Gln Asp Leu Asp Ile Pro Ile Leu Trp
145                 150                 155                 160

Arg Pro Leu His Glu Ala Glu Gly Gly Trp Phe Trp Trp Gly Ala Lys
                165                 170                 175

Gly Pro Glu Ala Cys Ile Ala Leu Tyr Arg Leu Met Phe Asp Arg Met
                180                 185                 190

Thr Asn His His Gly Leu Asn Asn Leu Leu Trp Val Trp Asn Ser Val
            195                 200                 205

Asp Pro Ser Trp Tyr Pro Gly Asn Asp Val Val Asp Ile Val Ser Ala
        210                 215                 220

Asp Ile Tyr Ala Asp Ala Gly Asp His Ser Pro Gln Glu Thr Phe
225                 230                 235                 240

Ala Ser Leu Gln Ser Leu Thr Gly Asp Thr Lys Leu Val Ala Leu Gly
                245                 250                 255

Glu Val Gly Asn Ile Pro Asp Pro Ala Ser Thr Gly Val Ala Asp
                260                 265                 270

Trp Ala Tyr Trp Val Thr Trp Asn Gly Asp Phe Ile Lys Gly Glu Asp
            275                 280                 285

Tyr Asn Pro Leu Glu Tyr Lys Lys Glu Val Phe Ser Ala Glu Asn Ile
        290                 295                 300

Ile Thr Arg Asp Glu Val Asp Val
305              310

<210> SEQ ID NO 31
<211> LENGTH: 327
<212> TYPE: PRT
<213> ORGANISM: Myrothecium roridum

<400> SEQUENCE: 31

Gly Thr Ile Glu Asn Arg Gln Trp Leu Thr Tyr Asn Pro Val Asp Ser
1               5                   10                  15

Ala Ala Thr Thr Glu Ala Arg Ala Leu Leu Arg Tyr Ile Gln Ser Gln
                20                  25                  30

Tyr Gly Trp Arg Tyr Leu Ser Gly Gln Gln Glu Arg Ala Glu Val Gln
            35                  40                  45

Trp Leu Lys Ser Asn Ile Gly Lys Thr Pro Ala Ile Gln Gly Ser Asp
    50                  55                  60

Leu Ile Asp Tyr Ser Pro Ser Arg Val Ser Tyr Gly Ala Thr Ser Thr
65                  70                  75                  80

Ala Val Glu Asp Ala Ile Ala Phe Asp Arg Gln Gly Gly Ile Val Thr
                85                  90                  95

Phe Thr Trp His Trp Asn Ala Pro Asn Cys Leu Tyr Asn Ser Ala Asp
            100                 105                 110

Gln Pro Trp Tyr Phe Gly Phe Tyr Thr Lys Ala Thr Cys Phe Asn Ile
        115                 120                 125

Gln Ala Ala Leu Ala Gln Gly Ser Asn Gly Ala Asp Tyr Lys Leu Leu
    130                 135                 140

Ile Arg Asp Ile Asp Ala Ile Ala Val Gln Leu Lys Arg Leu Arg Asp
145                 150                 155                 160

Ala Lys Val Pro Ile Leu Phe Arg Pro Leu His Glu Pro Asp Gly Ala
                165                 170                 175

Trp Phe Trp Trp Gly Ala Lys Gly Ser Gly Pro Phe Lys Gln Leu Trp
            180                 185                 190

Asp Ile Leu Tyr Asp Arg Leu Thr Lys Tyr His Gly Leu His Asn Met
        195                 200                 205

Leu Trp Val Cys Asn Thr Glu Lys Ser Asp Trp Tyr Pro Gly Asn Asn
    210                 215                 220

Lys Cys Asp Ile Ala Thr Thr Asp Val Tyr Val Asn Ala Gly Asp His
225                 230                 235                 240

Ser Val Gln Lys Ser His Trp Asp Ala Leu Tyr Gly Val Ser Gly Gly
                245                 250                 255

Gln Arg Ile Leu Ala Leu Gly Glu Val Gly Val Ile Pro Asp Pro Glu
            260                 265                 270

Arg Gln Ala Ser Glu Asn Val Pro Trp Ala Tyr Trp Met Thr Trp Asn
        275                 280                 285

Gly Tyr Phe Ile Arg Asp Gly Asn Tyr Asn Ser Arg Asn Phe Leu Gln
    290                 295                 300

Ser Thr Phe Ser Asn Ala Arg Val Val Thr Leu Asp Gly Thr Ser Pro
305                 310                 315                 320

Leu Gly Asn Trp Lys Ser Ser
                325

<210> SEQ ID NO 32
<211> LENGTH: 361
<212> TYPE: PRT
<213> ORGANISM: Aggregatibacter actinomycetemcomitans -continued

```
<400> SEQUENCE: 32

Asn Cys Cys Val Lys Gly Asn Ser Ile Tyr Pro Gln Lys Thr Ser Thr
1               5                   10                  15

Lys Gln Thr Gly Leu Met Leu Asp Ile Ala Arg His Phe Tyr Ser Pro
            20                  25                  30

Glu Val Ile Lys Ser Phe Ile Asp Thr Ile Ser Leu Ser Gly Gly Asn
        35                  40                  45

Phe Leu His Leu His Phe Ser Asp His Glu Asn Tyr Ala Ile Glu Ser
    50                  55                  60

His Leu Leu Asn Gln Arg Ala Glu Asn Ala Val Gln Gly Lys Asp Gly
65                  70                  75                  80

Ile Tyr Ile Asn Pro Tyr Thr Gly Lys Pro Phe Leu Ser Tyr Arg Gln
                85                  90                  95

Leu Asp Asp Ile Lys Ala Tyr Ala Lys Ala Lys Gly Ile Glu Leu Ile
            100                 105                 110

Pro Glu Leu Asp Ser Pro Asn His Met Thr Ala Ile Phe Lys Leu Val
            115                 120                 125

Gln Lys Asp Arg Gly Val Lys Tyr Leu Gln Gly Leu Lys Ser Arg Gln
        130                 135                 140

Val Asp Asp Glu Ile Asp Ile Thr Asn Ala Asp Ser Ile Thr Phe Met
145                 150                 155                 160

Gln Ser Leu Met Ser Glu Val Ile Asp Ile Phe Gly Asp Thr Ser Gln
                165                 170                 175

His Phe His Ile Gly Gly Asp Glu Phe Gly Tyr Ser Val Glu Ser Asn
            180                 185                 190

His Glu Phe Ile Thr Tyr Ala Asn Lys Leu Ser Tyr Phe Leu Glu Lys
        195                 200                 205

Lys Gly Leu Lys Thr Arg Met Trp Asn Asp Gly Leu Ile Lys Asn Thr
    210                 215                 220

Phe Glu Gln Ile Asn Pro Asn Ile Glu Ile Thr Tyr Trp Ser Tyr Asp
225                 230                 235                 240

Gly Asp Thr Gln Asp Lys Asn Glu Ala Ala Glu Arg Arg Asp Met Arg
                245                 250                 255

Val Ser Leu Pro Glu Leu Leu Ala Lys Gly Phe Thr Val Leu Asn Tyr
            260                 265                 270

Asn Ser Tyr Tyr Leu Tyr Ile Val Pro Lys Ala Ser Pro Thr Phe Ser
        275                 280                 285

Gln Asp Ala Ala Phe Ala Ala Lys Asp Val Ile Lys Asn Trp Asp Leu
    290                 295                 300

Gly Val Trp Asp Gly Arg Asn Thr Lys Asn Arg Val Gln Asn Thr His
305                 310                 315                 320

Glu Ile Ala Gly Ala Ala Leu Ser Ile Trp Gly Glu Asp Ala Lys Ala
                325                 330                 335

Leu Lys Asp Glu Thr Ile Gln Lys Asn Thr Lys Ser Leu Leu Glu Ala
            340                 345                 350

Val Ile His Lys Thr Asn Gly Asp Glu
        355                 360
```

CLEANING COMPOSITIONS INCLUDING ENZYMES

REFERENCE TO A SEQUENCE LISTING

This application contains a Sequence Listing in computer readable form, which is incorporated herein by reference.

FIELD OF THE INVENTION

The present disclosure relates to cleaning compositions comprising a specific glycoside hydrolase enzyme. The present disclosure also relates to methods of making and using such cleaning compositions. The present disclosure also relates to the use of the glycoside hydrolase enzyme.

BACKGROUND OF THE INVENTION

The detergent formulator is constantly aiming to improve the performance of detergent compositions. One particular challenge is the removal of certain soils of microbial origin from surfaces such as textiles. Such soils can be sticky and difficult to remove. Furthermore, because they are sticky they tend to adhere body soils and/or particulate soils to the surface, making soil removal difficult and tending to build up over time. This may be particularly noticeable for example on collars and cuffs where incomplete cleaning may occur.

Glycosyl hydrolases are enzymes that catalyze the hydrolysis of the glycosyl bond to release smaller sugars. There are over 100 classes of glycosyl hydrolase and many different enzymes fall within the class of glycosyl hydrolases, for example cellulases and xyloglucanases which can be used in cleaning compositions. Surprisingly, certain specific glycosyl hydrolases can provide particularly improved cleaning.

SUMMARY OF THE INVENTION

The present invention provides a cleaning and/or treatment composition comprising from 1 to 80 wt % of a surfactant system comprising anionic surfactant, an amylase enzyme and a glycosyl hydrolase enzyme having glycoside hydrolase activity, said glycosyl hydrolase enzyme being selected from:
  (i) first glycosyl hydrolases from the endo-alpha-1,4-polygalactosminidase class (EC 3.2.1.109) of enzymes;
  (ii) second glycosyl hydrolase enzymes from glycoside hydrolase family GH 39; and
  (iii) mixtures thereof.

A preferred first glycoside hydrolase enzyme having glycoside hydrolase activity is a variant having at least 60% identity or at least 65% or at least 70% or at least 75% or at least 80% or at least 85% or at least 90% or at least 95% identity up to 100% identity with SEQ ID NO:1.

A preferred second glycoside hydrolase having glycoside hydrolase activity has at least 60% identity to SEQ ID NO:1.

The present invention provides a method of cleaning a surface, such as a textile, that comprises mixing a cleaning composition as described herein with water to form an aqueous liquor and contacting a surface with the aqueous liquor, in a laundering step. Preferably the glycoside hydrolase enzyme is present in the aqueous wash liquor in an amount of from 0.01 ppm to 1000 ppm enzyme, based on active protein.

The present invention also relates to the use of a composition comprising an amylase enzyme and an enzyme having glycoside hydrolase activity and having at least 60% or at least 65% or at least 70% or at least 75% or at least 80% or at least 85% or at least 90% or at least 95% identity to 100% identity with SEQ ID NO:1, to enhance soil and/or stain removal and/or for malodour reduction, in particular for body soil removal.

DETAILED DESCRIPTION OF THE INVENTION

The components of the compositions and processes of the present disclosure are described in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein, the term "etheramine" includes the term "polyetheramine" and includes amines that have one or more ether groups.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the term "alkoxy" is intended to include C1-C8 alkoxy and C1-C8 alkoxy derivatives of polyols having repeating units such as butylene oxide, glycidol oxide, ethylene oxide or propylene oxide.

As used herein, unless otherwise specified, the terms "alkyl" and "alkyl capped" are intended to include C1-C18 alkyl groups, or even C1-C6 alkyl groups.

As used herein, unless otherwise specified, the term "aryl" is intended to include C3-12 aryl groups.

As used herein, unless otherwise specified, the term "arylalkyl" and "alkaryl" are equivalent and are each intended to include groups comprising an alkyl moiety bound to an aromatic moiety, typically having C1-C18 alkyl groups and, in one aspect, C1-C6 alkyl groups.

The terms "ethylene oxide," "propylene oxide" and "butylene oxide" may be shown herein by their typical designation of "EO," "PO" and "BO," respectively.

As used herein, the term "cleaning and/or treatment composition" includes, unless otherwise indicated, granular, powder, liquid, gel, paste, unit dose, bar form and/or flake type washing agents and/or fabric treatment compositions, including but not limited to products for laundering fabrics, fabric softening compositions, fabric enhancing compositions, fabric freshening compositions, and other products for the care and maintenance of fabrics, and combinations thereof. Such compositions may be pre-treatment compositions for use prior to a washing step or may be rinse added compositions, as well as cleaning auxiliaries, such as bleach additives and/or "stain-stick" or pre-treat compositions or substrate-laden products such as dryer added sheets.

As used herein, "cellulosic substrates" are intended to include any substrate which comprises cellulose, either 100% by weight cellulose or at least 20% by weight, or at least 30% by weight or at least 40 or at least 50% by weight or even at least 60% by weight cellulose. Cellulose may be found in wood, cotton, linen, jute, and hemp. Cellulosic substrates may be in the form of powders, fibers, pulp and articles formed from powders, fibers and pulp. Cellulosic fibers, include, without limitation, cotton, rayon (regenerated cellulose), acetate (cellulose acetate), triacetate (cellulose triacetate), and mixtures thereof. Typically, cellulosic substrates comprise cotton. Articles formed from cellulosic fibers include textile articles such as fabrics. Articles formed from pulp include paper.

As used herein, the term "maximum extinction coefficient" is intended to describe the molar extinction coefficient at the wavelength of maximum absorption (also referred to herein as the maximum wavelength), in the range of 400 nanometers to 750 nanometers.

As used herein "average molecular weight" is reported as a weight average molecular weight, as determined by its molecular weight distribution; as a consequence of their manufacturing process, polymers disclosed herein may contain a distribution of repeating units in their polymeric moiety.

As used herein the term "variant" refers to a polypeptide that contains an amino acid sequence that differs from a wild type or reference sequence. A variant polypeptide can differ from the wild type or reference sequence due to a deletion, insertion, or substitution of a nucleotide(s) relative to said reference or wild type nucleotide sequence. The reference or wild type sequence can be a full-length native polypeptide sequence or any other fragment of a full-length polypeptide sequence. A polypeptide variant generally has at least about 70% amino acid sequence identity with the reference sequence, but may include 75% amino acid sequence identity within the reference sequence, 80% amino acid sequence identity within the reference sequence, 85% amino acid sequence identity with the reference sequence, 86% amino acid sequence identity with the reference sequence, 87% amino acid sequence identity with the reference sequence, 88% amino acid sequence identity with the reference sequence, 89% amino acid sequence identity with the reference sequence, 90% amino acid sequence identity with the reference sequence, 91% amino acid sequence identity with the reference sequence, 92% amino acid sequence identity with the reference sequence, 93% amino acid sequence identity with the reference sequence, 94% amino acid sequence identity with the reference sequence, 95% amino acid sequence identity with the reference sequence, 96% amino acid sequence identity with the reference sequence, 97% amino acid sequence identity with the reference sequence, 98% amino acid sequence identity with the reference sequence, 98.5% amino acid sequence identity with the reference sequence or 99% amino acid sequence identity with the reference sequence.

As used herein, the term "solid" includes granular, powder, bar and tablet product forms.

As used herein, the term "fluid" includes liquid, gel, paste, and gas product forms.

Cleaning Composition

The present disclosure relates to cleaning and/or treatment compositions. The cleaning composition may be selected from the group of light duty liquid detergents compositions, heavy duty liquid detergent compositions, solid, for example powder detergent, hard surface cleaning compositions, detergent gels commonly used for laundry, bleaching compositions, laundry additives, fabric enhancer compositions, shampoos, body washes, other personal care compositions, and mixtures thereof. The cleaning composition may be a hard surface cleaning composition (such as a dishwashing composition) or a laundry composition (such as a heavy-duty liquid detergent composition).

The cleaning compositions may be in any suitable form. The composition can be selected from a liquid, solid, or combination thereof. As used herein, "liquid" includes free-flowing liquids, as well as pastes, gels, foams and mousses. Non-limiting examples of liquids include light duty and heavy duty liquid detergent compositions, fabric enhancers, detergent gels commonly used for laundry, bleach and laundry additives. Gases, e.g., suspended bubbles, or solids, e.g. particles, may be included within the liquids. A "solid" as used herein includes, but is not limited to, powders, agglomerates, and mixtures thereof. Non-limiting examples of solids include: granules, micro-capsules, beads, noodles, and pearlised balls. Solid compositions may provide a technical benefit including, but not limited to, through-the-wash benefits, pre-treatment benefits, and/or aesthetic effects.

The cleaning composition may be in the form of a unitized dose article, such as a tablet or in the form of a pouch. Such pouches typically include a water-soluble film, such as a polyvinyl alcohol water-soluble film, that at least partially encapsulates a composition. Suitable films are available from MonoSol, LLC (Indiana, USA). The composition can be encapsulated in a single or multi-compartment pouch. A multi-compartment pouch may have at least two, at least three, or at least four compartments. A multi-compartmented pouch may include compartments that are side-by-side and/or superposed. The composition contained in the pouch may be liquid, solid (such as powders), or combinations thereof.

Glycoside Hydrolase Enzyme

The enzyme essential to the present invention comprises a glycoside hydrolase having glycoside hydrolase activity selected from the group consisting of first glycosyl hydrolases described herein and second glycosyl hydrolases described herein and mixtures thereof.

First Glycosyl Hydrolases

First glycosyl hydrolases belong to the endo-alpha-1,4-polygalactosminidase class (EC 3.2.1.109) of enzymes, preferably having at least 60% or 65% or more preferably at least 70% or 75% or 80% or 85% or 90% or 95% up to 100% identity to SEQ ID NO:1.

Preferably the first glycoside hydrolase is from GH family 114.

Preferably, the first glycoside hydrolase enzyme is a microbial enzyme. The first glycoside hydrolase enzyme may be fungal or bacterial in origin. Bacterial glycoside hydrolases may be most preferred. Fungal glycoside hydrolases may be most preferred.

The first glycoside hydrolase may be obtainable from *Pseudomonas*, such as a *Pseudomonas aeruginosa*. Suitable examples from class EC 3.2.1.109 are described in Baker et al., (2016) Sci Adv, 2, such as the mature polypeptide SEQ ID NO: 1 of the present invention from *Pseudomonas aeruginosa*. Preferably the first glycoside hydrolase in the cleaning composition of the invention is PelAh.

Preferably the first glycoside hydrolase is an isolated glycoside hydrolase.

SecondGlycosyl Hydrolases

Second glycosyl hydrolases herein are selected from GH family 39. A preferred second glycosyl hydrolase comprises glycoside hydrolase enzyme having at least 60% or at least 65% or at least 70% or at least 75% or at least 80% or at least 85% or at least 90% or at least 95%, and less than or up to 100% identity to SEQ ID NO:13. Preferably, the second glycoside hydrolase enzyme comprises a microbial enzyme, which, may be fungal or bacterial in origin.

The second glycoside hydrolase may be obtainable from *Pseudomonas*, such as a *Pseudomonas aeruginosa*. Suitable examples are described in Baker et al., (2016) Sci Adv, 2, such as the mature polypeptide SEQ ID NO: 13 herein from *Pseudomonas aeruginosa*. A preferred second glycoside hydrolase in the cleaning composition of the invention is PslGh.

Preferably the glycoside hydrolase enzyme is present in the cleaning composition in an amount from 0.001 to 1 wt % based on active protein in the composition, or from 0.005 to 0.5 wt % or from 0.01 to 0.25 wt % based on weight of the composition.

Preferably the glycoside hydrolase enzyme is present in the laundering aqueous liquor in an amount of from 0.01 ppm to 1000 ppm enzyme, based on active protein or from 0.05 or from 0.1 ppm to 750 or 500 ppm.

The compositions and glycoside hydrolases described herein may also give rise to biofilm-disrupting effects or soil anti-redeposition effects.

Amylase Enzyme

The composition comprises an amylase enzyme. Suitable alpha-amylases include those of bacterial or fungal origin. Chemically or genetically modified mutants (variants) are included. A preferred alkaline alpha-amylase is derived from a strain of *Bacillus*, such as *Bacillus licheniformis*, *Bacillus amyloliquefaciens*, *Bacillus stearothermophilus*, *Bacillus subtilis*, or other *Bacillus* sp., such as *Bacillus* sp. NCIB 12289, NCIB 12512, NCIB 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) the variants described in WO 94/02597, WO 94/18314, WO 96/23874 and WO 97/43424, incorporated herein by reference especially the variants with substitutions in one or more of the following positions versus the enzyme having SEQ ID NO:2 herein 15, 23, 105, 106, 124, 128, 133, 154, 156, 181, 188, 190, 197, 202, 208, 209, 243, 264, 304, 305, 391, 408, and 444.

(b) the variants described in U.S. Pat. No. 5,856,164 and WO 99/23211, WO 96/23873, WO 00/60060 and WO 06/002643, incorporated herein by reference especially the variants with one or more substitutions in the following positions versus the AA560 enzyme: SEQ ID NO: 3 herein. 26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with SEQ ID NO: 4 herein, the wild-type enzyme from *Bacillus* SP722, especially variants with deletions in the 183 and 184 positions and variants described in WO 00/60060, which is incorporated herein by reference.

(d) variants exhibiting at least 95% identity with the wild-type enzyme from *Bacillus* sp. 707, SEQ ID NO: 5 herein, especially those comprising one or more of the following mutations M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations.

(e) variants exhibiting at least 90% identity with SEQ ID NO: 6 herein or SEQ ID NO: 7 herein, the wild-type enzyme from *Geobacillus Stearophermophilus* or a truncated version thereof;

(f) variants as described in EP 2540825 and EP 2357220, EP 2534233, which are incorporated herein by reference;

(g) variants as described in WO 2009100102 and WO 2010115028 which are incorporated herein by reference;

(h) variants exhibiting at least 89% identity with SEQ ID NO: 8 herein the amylases disclosed in WO2016091688, which is incorporated herein by reference, especially those comprising deletions at positions H183+G184 and additionally one or more mutations at positions 405, 421, 422 and/or 428.

(i) variants exhibiting at least 60% amino acid sequence identity with the "PcuAmyl α-amylase" from *Paenibacillus curdlanolyticus* YK9 SEQ ID NO: 9 herein.

(j) variants exhibiting at least 60% amino acid sequence identity with the "CspAmy2 amylase" from *Cytophaga* sp. SEQ ID NO: 10 herein.

(k) variants exhibiting at least 85% identity with AmyE from *Bacillus subtilis* SEQ ID NO: 11 herein.

(l) Variants exhibiting at least 90% identity variant with the wild-type amylase from *Bacillus* sp. KSM-K38 with accession number AB051102, SEQ ID NO: 12 herein.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE® and PURASTAR OXAM® (Genencor International Inc., Palo Alto, Calif.) and KAM® (Kao, 14-10 Nihonbashi Kayabacho, 1-chome, Chuo-ku Tokyo 103-8210, Japan). In one aspect, suitable amylases include NATALASE®, STAINZYME® and STAINZYME PLUS® and mixtures thereof.

Adjuncts

The cleaning compositions described herein may optionally include other adjunct components, for example fabric care benefit agent; additional enzyme; surfactant system; fabric shading dye; deposition aid; rheology modifier; builder; chelant; bleach; bleach activator, bleaching agent; bleach precursor; bleach booster; bleach catalyst; perfume and/or perfume microcapsules; perfume loaded zeolite;

starch encapsulated accord; polyglycerol esters; whitening agent; pearlescent agent; enzyme stabilizing systems; scavenging agents including fixing agents for anionic dyes, complexing agents for anionic surfactants, and mixtures thereof; optical brighteners or fluorescers; polymer including but not limited to soil release polymer and/or soil suspension polymer; dispersants; antifoam agents; non-aqueous solvent; fatty acid; suds suppressors, e.g., silicone suds suppressors; cationic starches; scum dispersants; substantive dyes; colorants; opacifier; antioxidant; hydrotropes such as toluenesulfonates, cumenesulfonates and naphthalenesulfonates; color speckles; colored beads, spheres or extrudates; clay softening agents; anti-bacterial agents, quaternary ammonium compounds. In particular, quaternary ammonium compounds may be present in particular for fabric enhancer compositions, such as fabric softeners, and comprise quaternary ammonium cations that are positively charged polyatomic ions of the structure $NR_4^+$, where R is an alkyl group or an aryl group.

Additional Enzymes

Preferably the composition of the invention comprises additional enzyme, for example selected from lipases, proteases, nucleases, galactanases, mannanases, pectate lyases, cellulases, cutinases, and mixtures thereof. The cleaning composition preferably comprises one or more additional enzymes selected from the group nucleases, galactanases, mannanases and mixtures thereof. Preferably in addition, the cleaning composition comprises one or more additional enzymes selected from proteases. Preferably the cleaning composition comprises one or more additional enzymes selected from lipases. The composition may comprise additional enzymes selected from the group of lipases, proteases, pectate lyases, cellulases, cutinases, and mixtures thereof. The composition may also comprise hemicellulases, peroxidases, xylanases, pectinases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, xanthan-degrading enzymes, further glycoside hydrolases and mixtures thereof. When present in the composition, the aforementioned additional enzymes may be present at levels from about 0.00001% to about 2%, from about 0.0001% to about 1% or even from about 0.001% to about 0.5% enzyme protein by weight of the composition.

Nucleases

In a preferred composition, the composition additionally comprises a nuclease enzyme. The nuclease enzyme is an enzyme capable of cleaving the phosphodiester bonds between the nucleotide sub-units of nucleic acids. Suitable nuclease enzymes may be deoxyribonuclease or ribonuclease enzyme or a functional fragment thereof. By functional fragment or part is meant the portion of the nuclease enzyme that catalyzes the cleavage of phosphodiester linkages in the DNA backbone and so is a region of said nuclease protein that retains catalytic activity. Thus, it includes truncated, but functional versions, of the enzyme and/or variants and/or derivatives and/or homologues whose functionality is maintained.

Preferably the nuclease enzyme is a deoxyribonuclease, preferably selected from any of the classes E.C. 3.1.21.x, where x=1, 2, 3, 4, 5, 6, 7, 8 or 9, E.C. 3.1.22.y where y=1, 2, 4 or 5, E.C. 3.1.30.z where z=1 or 2, E.C. 3.1.31.1 and mixtures thereof. Nuclease enzymes from class E.C. 3.1.21.x and especially where x=1 are particularly preferred. Nucleases in class E.C. 3.1.22.y cleave at the 5' hydroxyl to liberate 3' phosphomonoesters. Enzymes in class E.C. 3.1.30.z may be preferred as they act on both DNA and RNA and liberate 5'-phosphomonoesters. Suitable examples from class E.C. 3.1.31.2 are described in US2012/0135498A. Such enzymes are commercially available as DENARASE® enzyme from c-LECTA. Nuclease enzymes from class E.C. 3.1.31.1 produce 3'phosphomonoesters.

Preferably, the nuclease enzyme comprises a microbial enzyme. The nuclease enzyme may be fungal or bacterial in origin. Bacterial nucleases may be most preferred. Fungal nucleases may be most preferred.

The microbial nuclease is obtainable from *Bacillus*, such as a *Bacillus licheniformis* or *Bacillus subtilis* bacterial nucleases. A preferred nuclease is obtainable from *Bacillus licheniformis*, preferably from strain EI-34-6. A preferred deoxyribonuclease is a variant of *Bacillus licheniformis*, from strain EI-34-6 nucB deoxyribonuclease defined in SEQ ID NO:14 herein, or variant thereof, for example having at least 70% or 75% or 80% or 85% or 90% or 95%, 96%, 97%, 98%, 99% or 100% identical thereto. Other suitable nucleases are defined in SEQ ID NO:15 herein, or variant thereof, for example having at least 70% or 75% or 80% or 85% or 90% or 95%, 96%, 97%, 98%, 99% or 100% identical thereto. Other suitable nucleases are defined in SEQ ID NO:16 herein, or variant thereof, for example having at least 70% or 75% or 80% or 85% or 90% or 95%, 96%, 97%, 98%, 99% or 100% identical thereto.

A fungal nuclease is obtainable from *Aspergillus*, for example *Aspergillus oryzae*. A preferred nuclease is obtainable from *Aspergillus oryzae* defined in SEQ ID NO: 17 herein, or variant thereof, for example having at least 60% or 70% or 75% or 80% or 85% or 90% or 95%, 96%, 97%, 98%, 99% or 100% identical thereto.

Another suitable fungal nuclease is obtainable from *Trichoderma*, for example *Trichoderma harzianum*. A preferred nuclease is obtainable from *Trichoderma harzianum* defined in SEQ ID NO: 18 herein, or variant thereof, for example having at least 60% or 70% or 75% or 80% or 85% or 90% or 95%, 96%, 97%, 98%, 99% or 100% identical thereto.

Other fungal nucleases include those encoded by the DNA sequences of *Aspergillus oryzae* RIB40, *Aspergillus oryzae* 3.042, *Aspergillus flavus* NRRL3357, *Aspergillus parasiticus* SU-1, *Aspergillus nomius* NRRL13137, *Trichoderma reesei* QM6a, *Trichoderma virens* Gv29-8, *Oidiodendron maius* Zn, *Metarhizium guizhouense* ARSEF 977, *Metarhizium majus* ARSEF 297, *Metarhizium robertsii* ARSEF 23, *Metarhizium acridum* CQMa 102, *Metarhizium brunneum* ARSEF 3297, *Metarhizium anisopliae*, *Colletotrichum fioriniae* PJ7, *Colletotrichum sublineola*, *Trichoderma atroviride* IMI 206040, *Tolypocladium ophioglossoides* CBS 100239, *Beauveria bassiana* ARSEF 2860, *Colletotrichum higginsianum*, *Hirsutella minnesotensis* 3608, *Scedosporium apiospermum*, *Phaeomoniella chlamydospora*, *Fusarium verticillioides* 7600, *Fusarium oxysporum* f. sp. *cubense* race 4, *Colletotrichum graminicola* M1.001, *Fusarium oxysporum* FOSC 3-a, *Fusarium avenaceum*, *Fusarium langsethiae*, *Grosmannia clavigera* kw1407, *Claviceps purpurea* 20.1, *Verticillium longisporum*, *Fusarium oxysporum* f. sp. *cubense* race 1, *Magnaporthe oryzae* 70-15, *Beauveria bassiana* D1-5, *Fusarium pseudograminearum* CS3096, *Neonectria ditissima*, *Magnaporthiopsis poae* ATCC 64411, *Cordyceps militaris* CM01, *Marssonina brunnea* f. sp. 'multigermtubi' MB_m1, *Diaporthe ampelina*, *Metarhizium album* ARSEF 1941, *Colletotrichum gloeosporioides* Nara gc5, *Madurella mycetomatis*, *Metarhizium brunneum* ARSEF 3297, *Verticillium alfalfae* VaMs.102, *Gaeumannomyces graminis* var. *tritici* R3-111a-1, *Nectria haematococca* mpVI 77-13-4, *Verticil-*

*lium longisporum*, *Verticillium dahliae* VdLs.17, *Torrubiella hemipterigena*, *Verticillium longisporum*, *Verticillium dahliae* VdLs.17, *Botrytis cinerea* B05.10, *Chaetomium globosum* CBS 148.51, *Metarhizium anisopliae*, *Stemphylium lycopersici*, *Sclerotinia borealis* F-4157, *Metarhizium robertsii* ARSEF 23, *Myceliophthora thermophila* ATCC 42464, *Phaeosphaeria nodorum* SN15, *Phialophora attae*, *Ustilaginoidea virens*, *Diplodia seriata*, *Ophiostoma piceae* UAMH 11346, *Pseudogymnoascus pannorum* VKM F-4515 (FW-2607), *Bipolaris oryzae* ATCC 44560, *Metarhizium guizhouense* ARSEF 977, *Chaetomium thermophilum* var. *thermophilum* DSM 1495, *Pestalotiopsis fici* W106-1, *Bipolaris zeicola* 26-R-13, *Setosphaeria turcica* Et28A, *Arthroderma otae* CBS 113480 and *Pyrenophora tritici-repentis* Pt-1C-BFP.

Preferably the nuclease is an isolated nuclease.

Preferably the nuclease enzyme is present in the aqueous solution in an amount from 0.01 ppm to 1000 ppm of the nuclease enzyme, or from 0.05 or from 0.1 ppm to 750 or 500 ppm.

Galactanases

Preferably as an additional enzyme, the composition comprises a galactanase. Particularly preferred are the endo-beta-1,6-galactanase extracellular polymer-degrading enzyme. The term "endo-beta-1,6-galactanase" or "a polypeptide having endo-beta-1,6-galactanase activity" means an endo-beta-1,6-galactanase (EC 3.2.1.164) from the glycoside hydrolase family 30 that catalyzes the hydrolytic cleavage of 1,6-3-D-galactooligosaccharides with a degree of polymerization (DP) higher than 3, and their acidic derivatives with 4-O-methylglucosyluronate or glucosyluronate groups at the non-reducing terminals. For purposes of the present disclosure, endo-beta-1,6-galactanase activity is determined according to the procedure described in WO 2015185689 in Assay I, which is incorporated herein by reference. Suitable examples from class EC 3.2.1.164 are described in WO 2015185689, which is incorporated herein by reference. such as the mature polypeptide SEQ ID NO: 19 described herein.

Preferably the galactanase enzyme is s selected from Glycoside Hydrolase Family 30.

Preferably, the endo-beta-1,6-galactanase is a microbial enzyme. The endo-beta-1,6-galactanase may be fungal or bacterial in origin. Bacterial endo-beta-1,6-galactanase may be most preferred. Fungal endo-beta-1,6-galactanase may be most preferred.

A bacterial endo-beta-1,6-galactanase is obtainable from *Streptomyces*, for example *Streptomyces davawensis*. A preferred endo-beta-1,6-galactanase is obtainable from *Streptomyces davawensis* JCM 4913 defined in SEQ ID NO: 20 herein, or variant thereof, for example having at least 40% or 50% or 60% or 70% or 75% or 80% or 85% or 90% or 95%, 96%, 97%, 98%, 99% or 100% identical thereto.

Other bacterial endo-beta-1,6-galactanase include those encoded by the DNA sequences of *Streptomyces avermitilis* MA-4680 defined in SEQ ID NO: 21 herein, or variant thereof, for example having at least 40% or 50% or 60% or 70% or 75% or 80% or 85% or 90% or 95%, 96%, 97%, 98%, 99% or 100% identical thereto.

A fungal endo-beta-1,6-galactanase is obtainable from *Trichoderma*, for example *Trichoderma harzianum*. A preferred endo-beta-1,6-galactanase is obtainable from *Trichoderma harzianum* defined in SEQ ID NO: 22 herein, or variant thereof, for example having at least 40% or 50% or 60% or 70% or 75% or 80% or 85% or 90% or 95%, 96%, 97%, 98%, 99% or 100% identical thereto.

Other fungal endo-beta-1,6-galactanase include those encoded by the DNA sequences of *Ceratocystis fimbriata* f. sp. *Platani*, *Muscodor strobelii* WG-2009a, *Oculimacula yallundae*, *Trichoderma viride* GD36A, *Thermomyces stellatus*, *Myceliophthora thermophilia*.

Preferably the galactanase has an amino acid sequence having at least 60%, or at least 80%, or at least 90% or at least 95% identity with the amino acid sequence shown in SEQ ID NO: 23, SEQ ID NO: 24 or SEQ ID NO: 25.

Preferably the galactanase is an isolated galactanase.

Preferably the galactanase enzyme is present in the composition in an amount from 0.001 to 1 wt % based on active protein in the composition, or from 0.005 to 0.5 wt % or from 0.01 to 0.25 wt % based on the weight of the composition. Preferably the galactanase enzyme is present in the laundering aqueous solution in an amount of from 0.01 ppm to 1000 ppm of the galactanase enzyme, or from 0.05 or from 0.1 ppm to 750 or 500 ppm.

Mannanases

Preferably the composition comprises a mannanase enzyme. Mannanase enzymes are polypeptides having mannan endo-1,4-beta-mannosidase activity (EC 3.2.1.78) from the glycoside hydrolase family 26 that catalyzes the hydrolysis of 1,4-3-D-mannosidic linkages in mannans, galactomannans and glucomannans. Alternative names of mannan endo-1,4-beta-mannosidase are 1,4-3-D-mannan mannanohydrolase; endo-1,4-3-mannanase; endo-β-1,4-mannase; β-mannanase B; 3-1,4-mannan 4-mannanohydrolase; endo-3-mannanase; and β-D-mannanase. Preferred mannanases are members of the glycoside hydrolase family 26.

For purposes of the present disclosure, mannanase activity may be determined using the Reducing End Assay as described in the experimental section of WO 2015040159. Suitable examples from class EC 3.2.1.78 are described in WO 2015040159, such as the mature polypeptide SEQ ID NO: 26 described therein.

Preferred mannanases are variants having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide SEQ ID NO: 27 from *Ascobolus stictoideus*;

Preferred mannanases are variants having at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide SEQ ID NO: 28 from *Chaetomium virescens*.

Preferred mannanases are variants having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide SEQ ID NO: 29 from *Preussia aemulans*.

Preferred mannanases are variants having at least at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide SEQ ID NO: 30 from *Yunnania penicillata*.

Preferred mannanases are variants having at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide SEQ ID NO: 31 from *Myrothecium roridum*.

Preferably the mannanase is an isolated mannanase.

Preferably the mannanase enzyme is present in the cleaning compositions in an amount from 0.001 to 1 wt % based on active protein in the composition, or from 0.005 to 0.5 wt % or from 0.01 to 0.25 wt %. Preferably the mannanase enzyme is present in the laundering aqueous solution in an amount of from 0.01 ppm to 1000 ppm of the mannanase enzyme, or from 0.05 or from 0.1 ppm to 750 or 500 ppm.

The mannanases may also give rise to biofilm-disrupting effects.

Xanthan-Degrading Enzyme

The composition preferably comprises a xanthan-degrading enzyme. Xanthan gum is a polysaccharide secreted by the bacterium *Xanthomonas campestris*. Xanthan is composed of pentasaccharide subunits, forming a cellulose backbone with trisaccharide side chains composed of mannose-(beta 1, 4)-glucuronic-acid-(beta 1, 2)-mannose attached to alternate glucose residues in the backbone by alpha1,3 linkages. The cleaning composition preferably includes a xanthan degrading polypetide having xanthan lyase activity and/or endo-beta-1,4-glucanase activity. Xanthan lyases are enzymes that cleave the beta-D-mannosylalpha-beta-D-1,4-glucuronosyl bond of xanthan, preferably xanthan lyases isolated from *Paenibacillus alginolyticus* XL-1. Preferred xanthan-degrading enzymes are selected from the glycosyl hydrolase family 5 (GH5).

Acetylglucosaminidases

In a preferred composition, the composition may additionally comprise an acetylglucosaminidase enzyme, preferably a β-N-acetylglucosaminidase enzyme from E.C. 3.2.1.52, preferably an enzyme having at least 70%, or at least 75% or at least 80% or at least 85% or at least 90% or at least 95% or at least 96% or at least 97% or at least 98% or at least 99% or at least or 100% identity to SEQ ID NO:32.

Proteases

Preferably the composition comprises one or more proteases. Suitable proteases include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), preferably those derived from *Bacillus* sp., such as *B. lentus, B. alkalophilus, B. subtilis, B. amyloliquefaciens, B. pumilus* and *B. gibsonii* and *B. akibaii*.

(b) trypsin-type or chymotrypsin-type proteases, such as trypsin (e.g., of porcine or bovine origin), including the *Fusarium* protease and the chymotrypsin proteases derived from *Cellumonas*.

(c) metalloproteases, preferably those derived from *Bacillus amyloliquefaciens*; from *Bacillus, Brevibacillus, Thermoactinomyces, Geobacillus, Paenibacillus, Lysinibacillus* or *Streptomyces* spp.; from *Kribella alluminosa*; and from *Streptomyces* and *Lysobacter*.

(d) Protease having at least 90% identity to the subtilase from *Bacillus* sp. TY145, NCIMB 40339.

Preferred proteases include those derived from *Bacillus gibsonii* or *Bacillus Lentus*.

Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark), those sold under the tradename Maxatase®, Maxacal®, Maxapem®, Properase®, Purafect®, Purafect Prime®, Purafect Ox®, FN3®, FN4®, Excellase® and Purafect OXP® by Genencor International, those sold under the tradename Opticlean® and Optimase® by Solvay Enzymes, those available from Henkel/Kemira, namely BLAP having the following mutations S99D+S101R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D)—all from Henkel/Kemira; and KAP (*Bacillus alkalophilus* subtilisin with mutations A230V+S256G+S259N) from Kao.

Lipases

Preferably the composition comprises one or more lipases, including "first cycle lipases" such as those described in U.S. Pat. No. 6,939,702 B1 and U.S. Patent Application 2009/0217464. Preferred lipases are first-wash lipases. In one embodiment of the invention the composition comprises a first wash lipase. First wash lipases includes a lipase which is a polypeptide having an amino acid sequence which: (a) has at least 90% identity with the wild-type lipase derived from *Humicola lanuginosa* strain DSM 4109; (b) compared to said wild-type lipase, comprises a substitution of an electrically neutral or negatively charged amino acid at the surface of the three-dimensional structure within 15A of E1 or Q249 with a positively charged amino acid; and (c) comprises a peptide addition at the C-terminal; and/or (d) comprises a peptide addition at the N-terminal and/or (e) meets the following limitations: i) comprises a negative amino acid in position E210 of said wild-type lipase; ii) comprises a negatively charged amino acid in the region corresponding to positions 90-101 of said wild-type lipase; and iii) comprises a neutral or negative amino acid at a position corresponding to N94 or said wild-type lipase and/or has a negative or neutral net electric charge in the region corresponding to positions 90-101 of said wild-type lipase. Preferred are variants of the wild-type lipase from *Thermomyces lanuginosus* comprising one or more of the T231R and N233R mutations. The wild-type sequence is the 269 amino acids (amino acids 23-291) of the Swissprot accession number Swiss-Prot 059952 (derived from *Thermomyces lanuginosus* (*Humicola lanuginosa*)). Preferred lipases would include those sold under the tradenames Lipex® and Lipolex® and Lipoclean®.

Endoglucanases

Other preferred enzymes include microbial-derived endoglucanases exhibiting endo-beta-1,4-glucanase activity (E.C. 3.2.1.4), including a bacterial polypeptide endogenous to a member of the genus *Bacillus* and mixtures thereof.

Suitable endoglucanases are sold under the tradenames Celluclean® and Whitezyme® (Novozymes A/S, Bagsvaerd, Denmark).

Pectate Lyases

Other preferred enzymes include pectate lyases sold under the tradenames Pectawash®, Pectaway®, Xpect® and mannanases sold under the tradenames Mannaway® (all from Novozymes A/S, Bagsvaerd, Denmark), and Purabrite® (Genencor International Inc., Palo Alto, Calif.).

Surfactant System

The cleaning composition may comprise a surfactant system. The cleaning composition may comprise from about 1% to about 80%, or from 1% to about 60%, preferably from about 5% to about 50% more preferably from about 8% to about 40%, by weight of the cleaning composition, of a surfactant system.

Surfactants suitable for use in the surfactant system may be derived from natural and/or renewable sources.

The surfactant system may comprise an anionic surfactant, more preferably an anionic surfactant selected from the group consisting of, alkyl benzene sulfonate, alkyl sulfate, alkyl alkoxy sulfate, especially alkyl ethoxy sulfate, paraffin sulfonate and mixtures thereof, alkyl benzene sulfonates are particularly preferred. The surfactant system may further comprise a surfactant selected from the group consisting of nonionic surfactant, cationic surfactant, amphoteric surfactant, zwitterionic surfactant, and mixtures thereof. The surfactant system preferably comprises a nonionic surfactant, for example an ethoxylated nonionic surfactant. The surfactant system may comprise an amphoteric surfactant, for example an amine oxide surfactant, such as an alkyl dimethyl amine oxide. The surfactant system may comprise a zwitterionic surfactant, such as a betaine.

The most preferred surfactant system for the detergent composition of the present invention comprises from 1% to 40%, preferably 6% to 35%, more preferably 8% to 30% weight of the total composition of an anionic surfactant, preferably comprising an alkyl benzene sulphonate. The preferred surfactant system may optionally in addition comprise an alkyl alkoxy sulfate surfactant, more preferably an alkyl ethoxy sulfate, optionally combined with 0.5% to 15%, preferably from 1% to 12%, more preferably from 2% to 10% by weight of the composition of amphoteric and/or zwitterionic surfactant, more preferably an amphoteric and even more preferably an amine oxide surfactant, especially an alkyl dimethyl amine oxide. Most preferably the surfactant system comprises an anionic and a nonionic surfactant, preferably the weight ratio of the anionic to nonionic surfactant is from 25:1 to 1:2.

Anionic Surfactant

Anionic surfactants may be in salt form or acid form, typically in the form of a water-soluble odium, potassium, ammonium, magnesium or mono-, di- or tri-C2-C3 alkanolammonium salt, with the sodium cation being the usual one chosen.

Sulfonate Surfactant

Suitable anionic sulfonate surfactants for use herein include water-soluble salts of C8-C18 alkyl or hydroxyalkyl sulfonates; C11-C18 alkyl benzene sulfonates (LAS), modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548; methyl ester sulfonate (MES); and alpha-olefin sulfonate (AOS). Those also include the paraffin sulfonates may be monosulfonates and/or disulfonates, obtained by sulfonating paraffins of 10 to 20 carbon atoms. The sulfonate surfactant may also include the alkyl glyceryl sulfonate surfactants.

Sulfated Anionic Surfactant

Preferably the sulfated anionic surfactant is alkoxylated, more preferably, an alkoxylated branched sulfated anionic surfactant having an alkoxylation degree of from about 0.2 to about 4, even more preferably from about 0.3 to about 3, to about 4, even more preferably from about 0.4 to about 1.5 and especially from about 0.4 to about 1. Preferably, the alkoxy group is ethoxy. When the sulfated anionic surfactant is a mixture of sulfated anionic surfactants, the alkoxylation degree is the weight average alkoxylation degree of all the components of the mixture (weight average alkoxylation degree). In the weight average alkoxylation degree calculation the weight of sulfated anionic surfactant components not having alkoxylated groups should also be included.

Weight average alkoxylation degree=
($x1$*alkoxylation degree of surfactant
$1+x2$*alkoxylation degree of surfactant
$2+\ldots$)/($x1+x2+\ldots$)

wherein $x1$, $x2$, ... are the weights in grams of each sulfated anionic surfactant of the mixture and alkoxylation degree is the number of alkoxy groups in each sulfated anionic surfactant.

Preferably, the branching group is an alkyl. Typically, the alkyl is selected from methyl, ethyl, propyl, butyl, pentyl, cyclic alkyl groups and mixtures thereof. Single or multiple alkyl branches could be present on the main hydrocarbyl chain of the starting alcohol(s) used to produce the sulfated anionic surfactant used in the detergent of the invention. Most preferably the branched sulfated anionic surfactant is selected from alkyl sulfates, alkyl ethoxy sulfates, and mixtures thereof.

The branched sulfated anionic surfactant can be a single anionic surfactant or a mixture of anionic surfactants. In the case of a single surfactant the percentage of branching refers to the weight percentage of the hydrocarbyl chains that are branched in the original alcohol from which the surfactant is derived.

In the case of a surfactant mixture the percentage of branching is the weight average and it is defined according to the following formula:

Weight average of branching (%)=[($x1$*wt %
branched alcohol 1 in alcohol $1+x2$*wt %
branched alcohol 2 in alcohol $2+\ldots$)/($x1+$
$x2+\ldots$)]*100 wherein $x1$, $x2$, ... are the weight in grams of each alcohol in the total alcohol mixture of the alcohols which were used as starting material for the anionic surfactant for the detergent of the invention. In the weight average branching degree calculation, the weight of anionic surfactant components not having branched groups should also be included.

Suitable sulfate surfactants for use herein include water-soluble salts of C8-C18 alkyl or hydroxyalkyl, sulfate and/or ether sulfate. Suitable counterions include alkali metal cation or ammonium or substituted ammonium, but preferably sodium.

The sulfate surfactants may be selected from C8-C18 primary, branched chain and random alkyl sulfates (AS); C8-C18 secondary (2,3) alkyl sulfates; C8-C18 alkyl alkoxy sulfates (AExS) wherein preferably x is from 1-30 in which the alkoxy group could be selected from ethoxy, propoxy, butoxy or even higher alkoxy groups and mixtures thereof.

Alkyl sulfates and alkyl alkoxy sulfates are commercially available with a variety of chain lengths, ethoxylation and branching degrees. Commercially available sulfates include, those based on Neodol alcohols ex the Shell company, Lial-Isalchem and Safol ex the Sasol company, natural alcohols ex The Procter & Gamble Chemicals Company.

Preferred alkyl sulfates are those in which the anionic surfactant is an alkyl ethoxy sulfate with a degree of ethoxylation of from about 0.2 to about 3, more preferably from about 0.3 to about 2, even more preferably from about 0.4 to about 1.5, and especially from about 0.4 to about 1. They are also preferred anionic surfactant having a level of branching of from about 5% to about 40%, even more preferably from about 10% to 35% and especially from about 20% to 30%.

Nonionic Surfactant

Preferably the surfactant system comprises a nonionic surfactant, in an amount of from 0.1% to 40%, preferably 0.2% to 20%, most preferably 0.5% to 10% by weight of the composition. Suitable nonionic surfactants include the condensation products of aliphatic alcohols with from 1 to 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from 10 to 18 carbon atoms, preferably from 10 to 15 carbon atoms with from 2 to 18 moles, preferably 2 to 15, more preferably 5-12 of ethylene oxide per mole of alcohol. Highly preferred nonionic surfactants are the condensation products of guerbet alcohols with from 2 to 18 moles, preferably 2 to 15, more preferably 5-12 of ethylene oxide per mole of alcohol.

Other suitable non-ionic surfactants for use herein include fatty alcohol polyglycol ethers, alkylpolyglucosides and fatty acid glucamides.

Amphoteric Surfactant

The surfactant system may include amphoteric surfactant, such as amine oxide. Preferred amine oxides are alkyl dimethyl amine oxide or alkyl amido propyl dimethyl amine oxide, more preferably alkyl dimethyl amine oxide and especially coco dimethyl amino oxide. Amine oxide may have a linear or mid-branched alkyl moiety. Typical linear amine oxides include water-soluble amine oxides containing one R1 C8-18 alkyl moiety and 2 R2 and R3 moieties selected from the group consisting of C1-3 alkyl groups and C1-3 hydroxyalkyl groups. Preferably amine oxide is characterized by the formula R1-N(R2)(R3) O wherein R1 is a C8-18 alkyl and R2 and R3 are selected from the group consisting of methyl, ethyl, propyl, isopropyl, 2-hydroxethyl, 2-hydroxypropyl and 3-hydroxypropyl. The linear amine oxide surfactants in particular may include linear C10-C18 alkyl dimethyl amine oxides and linear C8-C12 alkoxy ethyl dihydroxy ethyl amine oxides. Preferred amine oxides include linear C10, linear C10-C12, and linear C12-C14 alkyl dimethyl amine oxides. As used herein "mid-branched" means that the amine oxide has one alkyl moiety having n1 carbon atoms with one alkyl branch on the alkyl moiety having n2 carbon atoms. The alkyl branch is located on the α carbon from the nitrogen on the alkyl moiety. This type of branching for the amine oxide is also known in the art as an internal amine oxide. The total sum of n1 and n2 is from 10 to 24 carbon atoms, preferably from 12 to 20, and more preferably from 10 to 16. The number of carbon atoms for the one alkyl moiety (n1) should be approximately the same number of carbon atoms as the one alkyl branch (n2) such that the one alkyl moiety and the one alkyl branch are symmetric. As used herein "symmetric" means that |n1−n2| is less than or equal to 5, preferably 4, most preferably from 0 to 4 carbon atoms in at least 50 wt %, more preferably at least 75 wt % to 100 wt % of the mid-branched amine oxides for use herein.

The amine oxide may further comprise two moieties, independently selected from a C1-3 alkyl, a C1-3 hydroxyalkyl group, or a polyethylene oxide group containing an average of from about 1 to about 3 ethylene oxide groups. Preferably the two moieties are selected from a C1-3 alkyl, more preferably both are selected as a C1 alkyl.

Zwitterionic Surfactant

Other suitable surfactants include betaines, such as alkyl betaines, alkylamidobetaine, amidazoliniumbetaine, sulfobetaine (INCI Sultaines) as well as the Phosphobetaine and preferably meets formula (I):

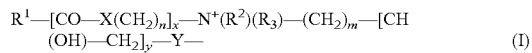

wherein

R$^1$ is a saturated or unsaturated C6-22 alkyl residue, preferably C8-18 alkyl residue, in particular a saturated C10-16 alkyl residue, for example a saturated C12-14 alkyl residue;

X is NH, NR$^4$ with C1-4 Alkyl residue R$^4$, O or S, n a number from 1 to 10, preferably 2 to 5, in particular 3, x 0 or 1, preferably 1, R$^2$, R$^3$ are independently a C1-4 alkyl residue, potentially hydroxy substituted such as a hydroxyethyl, preferably a methyl.

m a number from 1 to 4, in particular 1, 2 or 3, y 0 or 1 and

Y is COO, SO3, OPO(OR$^5$)O or P(O)(OR$^5$)O, whereby R$^5$ is a hydrogen atom H or a C1-4 alkyl residue.

Preferred betaines are the alkyl betaines of the formula (Ia), the alkyl amido propyl betaine of the formula (Ib), the Sulfo betaines of the formula (Ic) and the Amido sulfobetaine of the formula (Id);

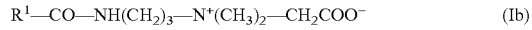

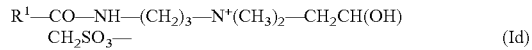

in which R$^1$1 as the same meaning as in formula I. Particularly preferred betaines are the Carbobetaine [wherein Y$^-$=COO$^-$], in particular the Carbobetaine of the formula (Ia) and (Ib), more preferred are the Alkylamidobetaine of the formula (Ib).

Examples of suitable betaines and sulfobetaine are the following [designated in accordance with INCI]: Almondamidopropyl of betaines, Apricotam idopropyl betaines, Avocadamidopropyl of betaines, Babassuamidopropyl of betaines, Behenam idopropyl betaines, Behenyl of betaines, betaines, Canolam idopropyl betaines, Capryl/Capram idopropyl betaines, Carnitine, Cetyl of betaines, Cocamidoethyl of betaines, Cocam idopropyl betaines, Cocam idopropyl Hydroxysultaine, Coco betaines, Coco Hydroxysultaine, Coco/Oleam idopropyl betaines, Coco Sultaine, Decyl of betaines, Dihydroxyethyl Oleyl Glycinate, Dihydroxyethyl Soy Glycinate, Dihydroxyethyl Stearyl Glycinate, Dihydroxyethyl Tallow Glycinate, Dimethicone Propyl of PG-betaines, Erucam idopropyl Hydroxysultaine, Hydrogenated Tallow of betaines, Isostearam idopropyl betaines, Lauram idopropyl betaines, Lauryl of betaines, Lauryl Hydroxysultaine, Lauryl Sultaine, Milk=idopropyl betaines, Minkamidopropyl of betaines, Myristam idopropyl betaines, Myristyl of betaines, Oleam idopropyl betaines, Oleam idopropyl Hydroxysultaine, Oleyl of betaines, Olivamidopropyl of betaines, Palmam idopropyl betaines, Palm itam idopropyl betaines, Palmitoyl Carnitine, Palm Kernelam idopropyl betaines, Polytetrafluoroethylene Acetoxypropyl of betaines, Ricinoleam idopropyl betaines, Sesam idopropyl betaines, Soyam idopropyl betaines, Stearam idopropyl betaines, Stearyl of betaines, Tallowam idopropyl betaines, Tallowam idopropyl Hydroxysultaine, Tallow of betaines, Tallow Dihydroxyethyl of betaines, Undecylenam idopropyl betaines and Wheat Germam idopropyl betaines. A preferred betaine is, for example, Cocoamidopropylbetaine.

Fatty Acid

Especially when in liquid form, preferably, the detergent composition comprises between 1.5% and 20%, more preferably between 2% and 15%, even more preferably between 3% and 10%, most preferably between 4% and 8% by weight of the liquid detergent composition of soap, preferably a fatty acid salt, more preferably an amine neutralized fatty acid salt, wherein preferably the amine is an alkanolamine more preferably selected from monoethanolamine, diethanolamine, triethanolamine or a mixture thereof, more preferably monoethanolamine.

Perfume

Preferred compositions of the invention comprise perfume. Typically, the composition comprises a perfume that comprises one or more perfume raw materials, selected from the group as described in WO 08/87497. However, any perfume useful in a detergent may be used. A preferred method of incorporating perfume into the compositions of the invention is via an encapsulated perfume particle comprising either a water-soluble hydroxylic compound or melamine-formaldehyde or modified polyvinyl alcohol. In one aspect, the encapsulate comprises (a) an at least partially water-soluble solid matrix comprising one or more water-soluble hydroxylic compounds, preferably starch; and (b) a perfume oil encapsulated by the solid matrix. In a further aspect, the perfume may be pre-complexed with a polyamine, preferably a polyethylenimine so as to form a Schiff base.

Polymers

The detergent composition may comprise one or more polymers for example for cleaning and/or care. Examples are optionally modified carboxymethylcellulose, poly (ethylene glycol), poly(vinyl alcohol), polycarboxylates such as polyacrylates, maleic/acrylic acid copolymers and lauryl methacrylate/acrylic acid co-polymers and carboxylate polymers.

Suitable carboxylate polymers include maleate/acrylate random copolymer or polyacrylate homopolymer. The carboxylate polymer may be a polyacrylate homopolymer having a molecular weight of from 4,000 Da to 9,000 Da, or from 6,000 Da to 9,000 Da. Other suitable carboxylate polymers are co-polymers of maleic acid and acrylic acid, and may have a molecular weight in the range of from 4,000 Da to 90,000 Da.

Other suitable carboxylate polymers are co-polymers comprising: (i) from 50 to less than 98 wt % structural units derived from one or more monomers comprising carboxyl groups; (ii) from 1 to less than 49 wt % structural units derived from one or more monomers comprising sulfonate moieties; and (iii) from 1 to 49 wt % structural units derived from one or more types of monomers selected from ether bond-containing monomers represented by formulas (I) and (II):

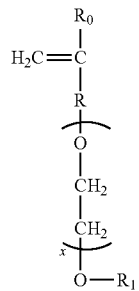

formula (I)

wherein in formula (I), $R_0$ represents a hydrogen atom or $CH_3$ group, R represents a $CH_2$ group, $CH_2CH_2$ group or single bond, X represents a number 0-5 provided X represents a number 1-5 when R is a single bond, and $R_1$ is a hydrogen atom or C1 to C20 organic group;

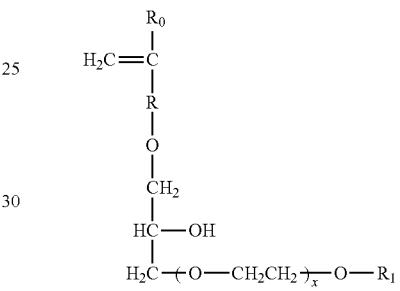

formula (II)

in formula (II), $R_0$ represents a hydrogen atom or $CH_3$ group, R represents a $CH_2$ group, $CH_2CH_2$ group or single bond, X represents a number 0-5, and $R_1$ is a hydrogen atom or C1 to C20 organic group.

The composition may comprise one or more amphiphilic cleaning polymers such as the compound having the following general structure: $bis((C_2H_5O)(C_2H_4O)_n)(CH_3)$—$N^+$—$C_xH_{2x}$—$N^+$—$(CH_3)$-$bis((C_2H_5O)(C_2H_4O)_n)$, wherein n=from 20 to 30, and x=from 3 to 8, or sulphated or sulphonated variants thereof. In one aspect, this polymer is sulphated or sulphonated to provide a zwitterionic soil suspension polymer.

The composition preferably comprises amphiphilic alkoxylated grease cleaning polymers which have balanced hydrophilic and properties such that they remove grease particles from fabrics and surfaces. Preferred amphiphilic alkoxylated grease cleaning polymers comprise a core structure and a plurality of alkoxylate groups attached to that core structure. These may comprise alkoxylated polyalkylenimines, preferably having an inner polyethylene oxide block and an outer polypropylene oxide block. Typically, these may be incorporated into the compositions of the invention in amounts of from 0.005 to 10 wt %, generally from 0.5 to 8 wt %.

Alkoxylated polycarboxylates such as those prepared from polyacrylates are useful herein to provide additional grease removal performance. Such materials are described in WO 91/08281 and PCT 90/01815. Chemically, these materials comprise polyacrylates having one ethoxy side-chain per every 7-8 acrylate units. The side-chains are of the formula —$(CH_2CH_2O)_m(CH_2)_nCH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

The composition may comprise polyethylene glycol polymers and these may be particularly preferred in compositions comprising mixed surfactant systems. Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, C1-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22.

Typically, these polymers when present are each incorporated into the compositions of the invention in amounts from 0.005 to 10 wt %, more usually from 0.05 to 8 wt %.

Preferably the composition comprises one or more carboxylate polymer, such as a maleate/acrylate random copolymer or polyacrylate homopolymer. In one aspect, the carboxylate polymer is a polyacrylate homopolymer having a molecular weight of from 4,000 Da to 9,000 Da, or from 6,000 Da to 9,000 Da. Typically, these are incorporated into the compositions of the invention in amounts from 0.005 to 10 wt %, or from 0.05 to 8 wt %.

Preferably the composition comprises one or more soil release polymers.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN260, SRN300 and SRN325 supplied by Clariant. Other suitable soil release polymers are Marloquest polymers, such as Marloquest SL supplied by Sasol.

Preferably the composition comprises one or more cellulosic polymer, including those selected from alkyl cellulose, alkyl alkoxyalkyl cellulose, carboxyalkyl cellulose, alkyl carboxyalkyl cellulose. Preferred cellulosic polymers are selected from the group comprising carboxymethyl cellulose, methyl cellulose, methyl hydroxyethyl cellulose, methyl carboxymethyl cellulose, and mixures thereof. In one aspect, the carboxymethyl cellulose has a degree of carboxymethyl substitution from 0.5 to 0.9 and a molecular weight from 100,000 Da to 300,000 Da.

The composition preferably comprises a cationically-modified polysaccharide polymer. Preferably, the cationic polysaccharide polymer is selected from cationically modified hydroxyethyl cellulose, cationically modified hydroxypropyl cellulose, cationically and hydrophobically modified hydroxyethyl cellulose, cationically and hydrophobically modified hydroxypropyl cellulose, or a mixture thereof, more preferably cationically modified hydroxyethyl cellulose, cationically and hydrophobically modified hydroxyethyl cellulose, or a mixture thereof.

Amines

The cleaning compositions described herein may contain an amine. The cleaning compositions may include from about 0.1% to about 10%, or from about 0.2% to about 5%, or from about 0.5% to about 4%, or from about 0.1% to about 4%, or from about 0.1% to about 2%, by weight of the composition, of an amine. The amine can be subjected to protonation depending on the pH of the cleaning medium in which it is used. Non-limiting examples of amines include, but are not limited to, etheramines, cyclic amines, polyamines, oligoamines (e.g., triamines, diamines, pentamines, tetraamines), or combinations thereof. The compositions described herein may comprise an amine selected from the group consisting of oligoamines, etheramines, cyclic amines, and combinations thereof. In some aspects, the amine is not an alkanolamine. In some aspects, the amine is not a polyalkyleneimine. Examples of suitable oligoamines include tetraethylenepentamine, triethylenetetraamine, diethylenetriamine, and mixtures thereof. Etheramines and cyclic amines may be particularly preferred.

Fabric Shading Dye

The composition may comprise a fabric shading agent. Suitable fabric shading agents include dyes, dye-clay conjugates, and pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof. Preferred dyes include alkoxylated azothiophenes, Solvent Violet 13, Acid Violet 50 and Direct Violet 9. Particularly preferred dyes are polymeric dyes, particularly comprising polyalkoxy, most preferably polyethoxy groups, for example:

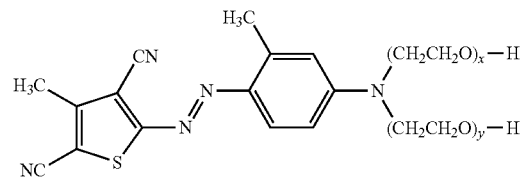

wherein the index values x and y are independently selected from 1 to 10.

Dye Transfer Inhibitors

Suitable dye transfer inhibitors include polyamine N-oxide polymers, copolymers of N-vinylpyrrolidone and N-vinylimidazole, polyvinylpyrrolidone, polyvinyloxazolidone, polyvinylimidazole and mixtures thereof. Preferred are poly (vinyl pyrrolidone), poly(vinylpyridine betaine), poly(vinylpyridine N-oxide), poly(vinyl pyrrolidone-vinyl imidazole) and mixtures thereof. Suitable commercially available dye transfer inhibitors include PVP-K15 and K30 (Ashland), Sokalan® HP165, HP50, HP53, HP59, HP56K, HP56, HP66 (BASF), Chromabond® S-400, 5403E and S-100 (Ashland).

Chelant

The composition may comprise chelant for example selected from phosphonic, sulphonic, succinic and acetic chelants or mixtures thereof. Suitable examples include HEDP, DTPA, EDTA, MGDA, GLDA, EDDS and 4,5-dihydroxy-1,3-benzenedisulfonic acids and salts thereof.

Methods of Making the Composition

The present disclosure relates to methods of making the compositions described herein. The compositions of the invention may be solid (for example granules or tablets) or liquid form. It may be preferred for the compositions to be in liquid form. They may be made by any process chosen by the formulator, including by a batch process, a continuous loop process, or combinations thereof.

When in the form of a liquid, the compositions of the invention may be aqueous (typically above 2 wt % or even above 5 or 10 wt % total water, up to 90 or up to 80 wt % or 70 wt % total water) or non-aqueous (typically below 2 wt % total water content). Typically, the compositions of the invention will be in the form of an aqueous solution or uniform dispersion or suspension of optical brightener, DTI and optional additional adjunct materials, some of which may normally be in solid form, that have been combined with the normally liquid components of the composition, such as the liquid alcohol ethoxylate nonionic, the aqueous liquid carrier, and any other normally liquid optional ingredients. Such a solution, dispersion or suspension will be acceptably phase stable. When in the form of a liquid, the detergents of the invention preferably have viscosity from 1 to 1500 centipoises (1-1500 mPa*s), more preferably from 100 to 1000 centipoises (100-1000 mPa*s), and most preferably from 200 to 500 centipoises (200-500 mPa*s) at 20 s−1 and 21° C. Viscosity can be determined by conventional methods. Viscosity may be measured using an AR 550 rheometer from TA instruments using a plate steel spindle at 40 mm diameter and a gap size of 500 μm. The high shear viscosity at 20 s-1 and low shear viscosity at 0.05-1 can be obtained from a logarithmic shear rate sweep from 0.1-1 to 25-1 in 3 minutes time at 21 C. The preferred rheology described therein may be achieved using internal existing structuring with detergent ingredients or by employing an external rheology modifier. More preferably the detergents, such as detergent liquid compositions have a high shear rate viscosity of from about 100 centipoise to 1500 centipoise, more preferably from 100 to 1000 cps. Unit Dose detergents, such as detergent liquid compositions have high shear rate viscosity of from 400 to 1000 cps. Detergents such as laundry softening compositions typically have high shear rate viscosity of from 10 to 1000, more preferably from 10 to 800 cps, most preferably from 10 to 500 cps. Hand dishwashing compositions have high shear rate viscosity of from 300 to 4000 cps, more preferably 300 to 1000 cps.

The cleaning and/or treatment compositions in the form of a liquid herein can be prepared by combining the components thereof in any convenient order and by mixing, e.g., agitating, the resulting component combination to form a phase stable liquid detergent composition. In a process for preparing such compositions, a liquid matrix is formed containing at least a major proportion, or even substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactants and the solid form ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme granulates, are incorporated. As a variation of the composition preparation procedure hereinbefore described, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

The adjunct ingredients in the compositions of this invention may be incorporated into the composition as the product of the synthesis generating such components, either with or without an intermediate purification step. Where there is no purification step, commonly the mixture used will comprise the desired component or mixtures thereof (and percentages given herein relate to the weight percent of the component itself unless otherwise specified) and in addition unreacted starting materials and impurities formed from side reactions and/or incomplete reaction. For example, for an ethoxylated or substituted component, the mixture will likely comprise different degrees of ethoxylation/substitution.

Method of Use

The present disclosure relates to a method of using the cleaning composition of the present disclosure to clean a surface, such as a textile. In general, the method includes mixing the cleaning composition as described herein with water to form an aqueous liquor and contacting a surface, preferably a textile, with the aqueous liquor in a laundering step. The target surface may include a greasy soil or body soil The present invention also provides use of a composition comprising an amylase enzyme and an enzyme having glycoside hydrolase activity belonging to the endo-alpha-1,4-polygalactosminidase class (EC 3.2.1.109) of enzymes for enhanced stain removal from a surface, preferably a fabric surface, particularly greasy stain or body soil removal and/or for reducing malodour. Preferably the glycoside hydrolase enzyme is a variant having at least 60% or 65% or 70% or 75% or 80% or 85% or 90% or 95% identity to 100% SEQ ID NO:1. Typically contact of the glycoside hydrolase enzyme with the surface will be in a laundering process in which the glycoside hydrolase enzyme or composition comprising the glycoside hydrolase enzyme is mixed with water to provide a wash liquor which is contacted with the surface.

The compositions of this invention, typically prepared as hereinbefore described, can be used to form aqueous (washing/treatment) liquor for use in the laundering/treatment of fabrics and/or hard surfaces. Generally, an effective amount of such a composition is added to water, for example in a conventional fabric automatic washing machine, to form such aqueousliquor. The aqueous liquor so formed is then contacted, typically under agitation, with the fabrics to be laundered/treated therewith. An effective amount of the cleaning composition herein added to water to form aqueous liquor can comprise amounts sufficient to form from about 500 to 25,000 ppm, or from 500 to 15,000 ppm of composition in the aqueousliquor, or from about 1,000 to 3,000 ppm of the cleaning composition herein will be provided in aqueous liquor.

Typically, the aqueous liquor is formed by contacting the cleaning composition with wash water in such an amount so that the concentration of the anionic surfactant in the wash liquor is from above 0.1 g/l to 5 g/l, or from 1 g/l, and to 4.5 g/l, or to 4.0 g/l, or to 3.5 g/l, or to 3.0 g/l, or to 2.5 g/l, or even to 2.0 g/l, or even to 1.5 g/l. The method of laundering fabric or textile may be carried out in a top-loading or front-loading automatic washing machine, or can be used in a hand-wash laundry application. In these applications, the aqueous liquor formed and concentration of cleaning composition in the wash liquor is that of the main wash cycle. Any input of water during any optional rinsing step(s) is not included when determining the volume of the aqueous liquor.

The aqueous liquor may comprise 40 litres or less of water, or 30 litres or less, or 20 litres or less, or 10 litres or less, or 8 litres or less, or even 6 litres or less of water. The aqueous liquor may comprise from above 0 to 15 litres, or from 2 litres, and to 12 litres, or even to 8 litres of water. Typically, from 0.01 kg to 2 kg of fabric per litre of aqueous liquor is dosed into said aqueous liquor. Typically, from 0.01 kg, or from 0.05 kg, or from 0.07 kg, or from 0.10 kg, or from 0.15 kg, or from 0.20 kg, or from 0.25 kg fabric per litre of aqueous liquor is dosed into said aqueous liquor. Optionally, 50 g or less, or 45 g or less, or 40 g or less, or 35 g or less, or 30 g or less, or 25 g or less, or 20 g or less, or even 15 g or less, or even 10 g or less of the composition is contacted to water to form the aqueous liquor. Such compositions are typically employed at concentrations of from about 500 ppm to about 15,000 ppm in solution. The water temperature typically ranges from about 5° C. to about 90° C. and, when laundering fabric, the water to fabric ratio is typically from about 1:1 to about 30:1. Typically the aqueous liquor comprising the cleaning composition of the invention has a pH of from 3 to 11.5.

In one aspect, such method comprises the steps of optionally washing and/or rinsing said surface or fabric, contacting said surface or fabric with any composition disclosed in this specification then optionally washing and/or rinsing said surface or fabric, with an optional drying step.

Drying of such surfaces or fabrics may be accomplished by any one of the common means employed either in domestic or industrial settings: machine drying or open-air drying. The fabric may comprise any fabric capable of being laundered in normal consumer or institutional use conditions, and the invention is particularly suitable for synthetic textiles such as polyester and nylon and especially for treatment of mixed fabrics and/or fibres comprising synthetic and cellulosic fabrics and/or fibres. As examples of synthetic fabrics are polyester, nylon, these may be present in mixtures with cellulosic fibres, for example, polycotton fabrics.

EXAMPLES

The following are illustrative examples of cleaning compositions according to the present disclosure and are not intended to be limiting.

Examples 1 to 18: Unit Dose Compositions

These examples provide various formulations for unit dose laundry detergents and comprise double compartment unit dose products comprising one powder and one liquid compartment. The film used to encapsulate the compositions in PVA. Each example is prepared by combining a liquid compartment composition selected from compositions A-E with a powder compartment composition selected from compositions F-K.

|  | Example | | | | | |
|---|---|---|---|---|---|---|
|  | 1 | 2 | 3 | 4 | 5 | 6 |
| Liquid composition | 20 g A | 25 g A | 20 g A | 15 g A | 20 g B | 20 g B |
| Solid composition | 15 g F | 12 g G | 12 g H | 12 g I | 15 g J | 15 g K |

|  | Example | | | | | |
|---|---|---|---|---|---|---|
|  | 7 | 8 | 9 | 10 | 11 | 12 |
| Liquid composition | 15 g B | 17 g B | 20 g C | 19 g C | 15 g C | 25 g C |
| Solid composition | 15 g L | 14 g F | 15 g G | 18 g H | 15 g I | 12 g J |

|  | Example | | | | | |
|---|---|---|---|---|---|---|
|  | 13 | 14 | 15 | 16 | 17 | 18 |
| Liquid composition | 20 g D | 18 g D | 22 g D | 32 g E | 32 g E | 27 g E |
| Solid composition | 20 g K | 13 g L | 15 g F | 17 g G | 12 g H | 18 g I |

| Ingredients | A | B | C | D | E |
|---|---|---|---|---|---|
|  | % weight of compartment | | | | |
| LAS | 19.09 | 16.76 | 8.59 | 6.56 | 3.44 |
| AE3S | 1.91 | 0.74 | 0.18 | 0.46 | 0.07 |
| AE7 | 14.00 | 17.50 | 26.33 | 28.08 | 31.59 |
| Citric Acid | 0.6 | 0.6 | 0.6 | 0.6 | 0.6 |
| C12-15 Fatty Acid | 14.8 | 14.8 | 14.8 | 14.8 | 14.8 |
| Polymer 3 | 4.0 | 4.0 | 4.0 | 4.0 | 4.0 |
| Chelant 2 | 1.2 | 1.2 | 1.2 | 1.2 | 1.2 |
| Optical Brightener 1 | 0.20 | 0.25 | 0.01 | 0.01 | 0.50 |
| Optical Brightener 2 | 0.20 | — | 0.25 | 0.03 | 0.01 |
| Optical Brightener 3 | 0.18 | 0.09 | 0.30 | 0.01 | — |
| DTI 1 | 0.10 | — | 0.20 | 0.01 | 0.05 |
| DTI 2 | — | 0.10 | 0.20 | 0.25 | 0.05 |
| Glycerol | 6.1 | 6.1 | 6.1 | 6.1 | 6.1 |
| Monoethanol amine | 8.0 | 8.0 | 8.0 | 8.0 | 8.0 |
| Tri-isopropanol amine | — | — | 2.0 | — | — |
| Tri-ethanol amine | — | 2.0 | — | — | — |
| Cumene sulfonate | — | — | — | — | 2.0 |
| Protease | 0.80 | 0.60 | 0.07 | 1.00 | 1.50 |
| Mannanase | 0.07 | 0.05 | 0.05 | 0.10 | 0.01 |
| Amylase 1 | 0.20 | 0.11 | 0.30 | 0.50 | 0.05 |
| Amylase 2 | 0.11 | 0.20 | 0.10 | — | 0.50 |
| Hydrolase of SEQ ID NO: 1(active protein) or SEQ ID NO: 13 (active protein) or combination thereof | 0.005 | 0.05 | 0.005 | 0.010 | 0.01 |
| Polishing enzyme | 0.005 | 0.05 | — | — | — |
| Nuclease | 0.005 | — | — | — | 0.005 |
| Dispersin B | 0.010 | 0.05 | 0.005 | 0.005 | — |
| Cyclohexyl dimethanol | — | — | — | 2.0 | — |
| Acid violet 50 | 0.03 | 0.02 |  |  |  |
| Violet DD |  |  | 0.01 | 0.05 | 0.02 |
| Structurant | 0.14 | 0.14 | 0.14 | 0.14 | 0.14 |
| Perfume | 1.9 | 1.9 | 1.9 | 1.9 | 1.9 |
| Water, solvents and miscellaneous | To 100% | | | | |
| pH | 7.5-8.2 | | | | |

| Ingredient | F | G | H | I | J | K |
|---|---|---|---|---|---|---|
|  | % weight | | | | | |
| Sodium carbonate | 20.0 | 35.0 | 30.0 | 29.0 | 28.0 | 18.0 |
| Carboxymethyl cellulose | 2.0 | 1.0 | — | — | 2.5 | 0.6 |
| Sodium silicate 2R | 5.0 | — | 5.0 | 3.2 | 20.0 | — |
| Tetraacetyl ethylenediamine | 20.0 | 15.0 | 18.0 | 15.0 | — | 25.0 |
| Sodium percarbonate | 50.0 | 44.0 | 45.0 | 45.0 | 29.0 | 50.0 |
| Polyetheramine | 0.5 | 2 | 0.5 | 1 | 0.5 | 4 |
| Sulfate/Water & Miscellaneous | Balance | | | | | |

Based on total cleaning and/or treatment composition/compartment weight. Enzyme levels are reported as raw material.

Examples 19 to 24

Granular laundry detergent compositions for hand washing or washing machines, typically top-loading washing machines.

| Ingredient | 19 | 20 | 21 | 22 | 23 | 24 |
|---|---|---|---|---|---|---|
| | % weight | | | | | |
| LAS | 11.33 | 10.81 | 7.04 | 4.20 | 3.92 | 2.29 |
| Quaternary ammonium | 0.70 | 0.20 | 1.00 | 0.60 | — | — |
| AE3S | 0.51 | 0.49 | 0.32 | — | 0.08 | 0.10 |
| AE7 | 8.36 | 11.50 | 12.54 | 11.20 | 16.00 | 21.51 |
| Sodium Tripolyphosphate | 5.0 | — | 4.0 | 9.0 | 2.0 | — |
| Zeolite A | — | 1.0 | — | 1.0 | 4.0 | 1.0 |
| Sodium silicate 1.6R | 7.0 | 5.0 | 2.0 | 3.0 | 3.0 | 5.0 |
| Sodium carbonate | 20.0 | 17.0 | 23.0 | 14.0 | 14.0 | 16.0 |
| Polyacrylate MW 4500 | 1.0 | 0.6 | 1.0 | 1.0 | 1.5 | 1.0 |
| Polymer 6 | 0.1 | 0.2 | — | — | 0.1 | — |
| Carboxymethyl cellulose | 1.0 | 0.3 | 1.0 | 1.0 | 1.0 | 1.0 |
| Acid Violet 50 | 0.05 | — | 0.02 | — | 0.04 | — |
| Violet DD | — | 0.03 | — | 0.03 | — | 0.03 |
| Protease 2 | 0.10 | 0.10 | 0.10 | 0.10 | — | 0.10 |
| Amylase | 0.03 | — | 0.03 | 0.03 | 0.03 | 0.03 |
| Lipase | 0.03 | 0.07 | 0.30 | 0.10 | 0.07 | 0.40 |
| Polishing enzyme | 0.002 | — | 0.05 | — | 0.02 | — |
| Hydrolase of SEQ ID NO: 1 (active protein) or SEQ ID NO: 13 (active protein) or combination thereof | 0.001 | 0.001 | 0.01 | 0.05 | 0.002 | 0.02 |
| Nuclease (as active protein) | 0.001 | — | — | — | 0.001 | — |
| Dispersin B | 0.001 | 0.001 | 0.05 | — | 0.001 | — |
| Optical Brightener 1 | 0.200 | 0.001 | 0.300 | 0.650 | 0.050 | 0.001 |
| Optical Brightener 2 | 0.060 | — | 0.650 | 0.180 | 0.200 | 0.060 |
| Optical Brightener 3 | 0.100 | 0.060 | 0.050 | — | 0.030 | 0.300 |
| Chelant 1 | 0.60 | 0.80 | 0.60 | 0.25 | 0.60 | 0.60 |
| DTI 1 | 0.32 | 0.15 | 0.15 | — | 0.10 | 0.10 |
| DTI 2 | 0.32 | 0.15 | 0.30 | 0.30 | 0.10 | 0.20 |
| Sodium Percarbonate | 4.6 | 5.2 | 5.0 | 5.7 | 4.5 | 7.3 |
| Nonanoyloxybenzensulfonate | 1.9 | 0.0 | 1.66 | 0.0 | 0.33 | 0.75 |
| Tetraacetylethylenediamine | 0.58 | 1.2 | 0.51 | 0.0 | 0.015 | 0.28 |
| Photobleach | 0.0030 | 0.0 | 0.0012 | 0.0030 | 0.0021 | — |
| S-ACMC | 0.1 | 0.0 | 0.0 | 0.0 | 0.06 | 0.0 |
| Polyetheramine | 0.5 | 2 | 0.5 | 1 | 0.5 | 4 |
| Sulfate/Moisture | Balance | | | | | |

Examples 25-30

Granular laundry detergent compositions typically for front-loading automatic washing machines.

| Ingredient | 25 | 26 | 27 | 28 | 29 | 30 |
|---|---|---|---|---|---|---|
| | % weight | | | | | |
| LAS | 6.08 | 5.05 | 4.27 | 3.24 | 2.30 | 1.09 |
| AE3S | — | 0.90 | 0.21 | 0.18 | — | 0.06 |
| AS | 0.34 | — | — | — | — | — |
| AE7 | 4.28 | 5.95 | 6.72 | 7.98 | 9.20 | 10.35 |
| Quaternary ammonium | 0.5 | — | — | 0.3 | — | — |
| Crystalline layered silicate | 4.1 | — | 4.8 | — | — | — |
| Zeolite A | 5.0 | — | 2.0 | — | 2.0 | 2.0 |
| Citric acid | 3.0 | 4.0 | 3.0 | 4.0 | 2.5 | 3.0 |
| Sodium carbonate | 11.0 | 17.0 | 12.0 | 15.0 | 18.0 | 18.0 |
| Sodium silicate 2R | 0.08 | — | 0.11 | — | — | — |
| Optical Brightener 1 | — | 0.25 | 0.05 | 0.01 | 0.10 | 0.02 |
| Optical Brightener 2 | — | — | 0.25 | 0.20 | 0.01 | 0.08 |
| Optical Brightener 3 | — | 0.06 | 0.04 | 0.15 | — | 0.05 |
| DTI 1 | 0.08 | — | 0.04 | — | 0.10 | 0.01 |
| DTI 2 | 0.08 | — | 0.04 | 0.10 | 0.10 | 0.02 |
| Soil release agent | 0.75 | 0.72 | 0.71 | 0.72 | — | — |
| Acrylic/maleic acid copolymer | 1.1 | 3.7 | 1.0 | 3.7 | 2.6 | 3.8 |
| Carboxymethyl cellulose | 0.2 | 1.4 | 0.2 | 1.4 | 1.0 | 0.5 |
| Protease 3 | 0.20 | 0.20 | 0.30 | 0.15 | 0.12 | 0.13 |

| Ingredient | 25 | 26 | 27 | 28 | 29 | 30 |
|---|---|---|---|---|---|---|
| | | | % weight | | | |
| Amylase 3 | 0.20 | 0.15 | 0.20 | 0.30 | 0.15 | 0.15 |
| Lipase | 0.05 | 0.15 | 0.10 | — | — | — |
| Amylase 2 | 0.03 | 0.07 | — | — | 0.05 | 0.05 |
| Cellulase 2 | — | — | — | — | 0.10 | 0.10 |
| Polishing enzyme | 0.003 | 0.005 | 0.020 | — | — | — |
| Hydrolase of SEQ ID NO: 1 (active protein) or SEQ ID NO: 13 (active protein) or combination thereof | 0.002 | 0.010 | 0.020 | 0.020 | 0.020 | 0.003 |
| Nuclease | — | — | — | — | 0.005 | 0.005 |
| Dispersin B | 0.002 | — | 0.020 | 0.020 | — | — |
| Tetraacetylehtylenediamine | 3.6 | 4.0 | 3.6 | 4.0 | 2.2 | 1.4 |
| Sodium percarbonate | 13.0 | 13.2 | 13.0 | 13.2 | 16.0 | 14.0 |
| Chelant 3 | — | 0.2 | — | 0.2 | — | 0.2 |
| Chelant 2 | 0.2 | — | 0.2 | — | 0.2 | 0.2 |
| MgSO$_4$ | — | 0.42 | — | 0.42 | — | 0.4 |
| Perfume | 0.5 | 0.6 | 0.5 | 0.6 | 0.6 | 0.6 |
| Suds suppressor agglomerate | 0.05 | 0.10 | 0.05 | 0.10 | 0.06 | 0.05 |
| Soap | 0.45 | 0.45 | 0.45 | 0.45 | — | — |
| Acid Violet 50 | 0.04 | — | 0.05 | — | 0.04 | — |
| Violet DD | — | 0.04 | — | 0.05 | — | 0.04 |
| S-ACMC | 0.01 | 0.01 | — | 0.01 | — | — |
| Direct Violet 9 (active) | — | — | 0.0001 | 0.0001 | — | — |
| Polyetheramine | 0.5 | 2 | 0.5 | 1 | 0.5 | 4 |
| Sulfate/Water & Miscellaneous | | | Balance | | | |

Examples 31-37: Heavy Duty Liquid Laundry Detergent Compositions

| Ingredients | 31 | 32 | 33 | 34 | 35 | 36 | 37 |
|---|---|---|---|---|---|---|---|
| | | | | % weight | | | |
| AE$_{1.8}$S | 6.77 | 5.16 | 1.36 | 1.30 | — | — | — |
| AE$_3$S | — | — | — | — | 0.45 | — | — |
| LAS | 0.86 | 2.06 | 2.72 | 0.68 | 0.95 | 1.56 | 3.55 |
| HSAS | 1.85 | 2.63 | 1.02 | — | — | — | — |
| AE9 | 6.32 | 9.85 | 10.20 | 7.92 | | | |
| AE8 | | | | | | | 35.45 |
| AE7 | | | | | 8.40 | 12.44 | |
| C$_{12-14}$ dimethyl Amine Oxide | 0.30 | 0.73 | 0.23 | 0.37 | — | — | — |
| C$_{12-18}$ Fatty Acid | 0.80 | 1.90 | 0.60 | 0.99 | 1.20 | — | 15.00 |
| Citric Acid | 2.50 | 3.96 | 1.88 | 1.98 | 0.90 | 2.50 | 0.60 |
| Optical Brightener 1 | 1.00 | 0.80 | 0.10 | 0.30 | 0.05 | 0.50 | 0.001 |
| Optical Brightener 3 | 0.001 | 0.05 | 0.01 | 0.20 | 0.50 | — | 1.00 |
| Sodium formate | 1.60 | 0.09 | 1.20 | 0.04 | 1.60 | 1.20 | 0.20 |
| DTI 1 | 0.32 | 0.05 | — | 0.60 | 0.10 | 0.60 | 0.01 |
| DTI 2 | 0.32 | 0.10 | 0.60 | 0.60 | 0.05 | 0.40 | 0.20 |
| Sodium hydroxide | 2.30 | 3.80 | 1.70 | 1.90 | 1.70 | 2.50 | 2.30 |
| Monoethanolamine | 1.40 | 1.49 | 1.00 | 0.70 | — | — | — |
| Diethylene glycol | 5.50 | — | 4.10 | — | — | — | — |
| Chelant 1 | 0.15 | 0.15 | 0.11 | 0.07 | 0.50 | 0.11 | 0.80 |
| 4-formyl-phenylboronic acid | — | — | — | — | 0.05 | 0.02 | 0.01 |
| Sodium tetraborate | 1.43 | 1.50 | 1.10 | 0.75 | — | 1.07 | — |
| Ethanol | 1.54 | 1.77 | 1.15 | 0.89 | — | 3.00 | 7.00 |
| Polymer 1 | 0.10 | — | — | — | — | — | 2.00 |
| Polymer 2 | 0.30 | 0.33 | 0.23 | 0.17 | — | — | — |
| Polymer 3 | — | — | — | — | — | — | 0.80 |
| Polymer 4 | 0.80 | 0.81 | 0.60 | 0.40 | 1.00 | 1.00 | — |
| 1,2-Propanediol | — | 6.60 | — | 3.30 | 0.50 | 2.00 | 8.00 |
| Structurant | 0.10 | — | — | — | — | — | 0.10 |
| Perfume | 1.60 | 1.10 | 1.00 | 0.80 | 0.90 | 1.50 | 1.60 |
| Perfume encapsulate | 0.10 | 0.05 | 0.01 | 0.02 | 0.10 | 0.05 | 0.10 |
| Protease | 0.80 | 0.60 | 0.70 | 0.90 | 0.70 | 0.60 | 1.50 |
| Hydrolase of SEQ ID NO: 1 (active protein) or SEQ ID NO: 13 (active protein) or combination thereof | 0.07 | 0.05 | 0.045 | 0.06 | 0.04 | 0.045 | 0.10 |
| Amylase 1 | 0.30 | — | 0.30 | 0.10 | — | 0.40 | 0.10 |
| Amylase 2 | — | 0.20 | 0.10 | 0.15 | 0.07 | — | 0.10 |
| Xyloglucanase | 0.20 | 0.10 | — | — | 0.05 | 0.05 | 0.20 |
| Lipase | 0.40 | 0.20 | 0.30 | 0.10 | 0.20 | — | — |
| Polishing enzyme | — | 0.04 | — | — | — | 0.004 | — |

-continued

| Ingredients | 31 | 32 | 33 | 34 % weight | 35 | 36 | 37 |
|---|---|---|---|---|---|---|---|
| Nuclease | 0.05 | 0.03 | 0.01 | 0.03 | 0.03 | 0.003 | 0.003 |
| Dispersin B | — | — | — | 0.05 | 0.03 | 0.001 | 0.001 |
| Acid Violet 50 | 0.05 | — | — | — | — | — | 0.005 |
| Direct Violet 9 | — | — | — | — | — | 0.05 | — |
| Violet DD | — | 0.035 | 0.02 | 0.037 | 0.04 | — | — |
| Water insoluble plant fiber | 0.2 | — | — | — | 1.2 | — | — |
| Dye control agent | — | 0.3 | — | 0.5 | — | 0.3 | — |
| Alkoxylated polyaryl/polyalkyl phenol | — | — | 1.2 | — | — | — | 3.1 |
| Water, dyes & minors | Balance | | | | | | |
| pH | 8.2 | | | | | | |

Based on total cleaning and/or treatment composition weight. Unless indicated otherwise, enzyme levels are reported as raw material.

AE1.8S is $C_{12\text{-}15}$ alkyl ethoxy sulfate with an average degree of ethoxylation of 1.8

AE3S is $C_{12\text{-}15}$ alkyl ethoxy sulfate with an average degree of ethoxylation of 1.8

AE7 is $C_{12\text{-}13}$ alcohol ethoxylate, with an average degree of ethoxylation of 7

AE8 is $C_{12\text{-}13}$ alcohol ethoxylate, with an average degree of ethoxylation of 8

AE9 is $C_{12\text{-}13}$ alcohol ethoxylate, with an average degree of ethoxylation of 9 Alkoxylated polyaryl is alkoxylated polyaryl/polyalkyl phenol for example Emulsogen® TS160, Hostapal® /polyalkyl phenol BV conc., Sapogenat® T110 or Sapogenat® T139, all from Clariant Amylase 1 is Stainzyme®, 15 mg active/g Amylase 2 is Natalase®, 29 mg active/g Amylase 3 is Stainzyme® Plus, 20 mg active/g, AS is $C_{12\text{-}14}$ alkylsulfate Cellulase 2 is Celluclean™, 15.6 mg active/g Xyloglucanase is Whitezyme®, 20 mg active/g Chelant 1 is diethylene triamine pentaacetic acid Chelant 2 is 1-hydroxyethane 1,1-diphosphonic acid Chelant 3 is sodium salt of ethylenediamine-N,N'-disuccinic acid, (S,S) isomer (EDDS)

Dispersin B is a glycoside hydrolase, reported as 1000 mg active/g

DTI 1 is poly(4-vinylpyridine-1-oxide) (such as Chromabond S-403E®),

DTI 2 is poly(l-vinylpyrrolidone-co-1-vinylimidazole) (such as Sokalan HP56®).

Dye Control Agent is for example Suparex® O.IN (M1), Nylofixan® P (M2), Nylofixan® PM (M3), or Nylofixan® HF (M4)

HSAS is mid-branched alkyl sulfate as disclosed in U.S. Pat. Nos. 6,020,303 and 6,060,443

LAS is linear alkylbenzenesulfonate having an average aliphatic carbon chain length $C_9\text{-}C_{15}$ (HLAS is acid form).

Lipase is Lipex®, 18 mg active/g

Mannanase is Mannaway®, 25 mg active/g

Nuclease is a Phosphodiesterase according to any of SEQ ID NOs: 14 to 18, preferably SEQ ID NO: 14, 15 or 16, reported as active protein Optical Brightener 1 is disodium 4,4'-bis{[4-anilino-6-morpholino-s-triazin-2-yl]-amino}-2,2'-stilbenedisulfonate Optical Brightener 2 is disodium 4,4'-bis-(2-sulfostyryl) biphenyl (sodium salt)

Optical Brightener 3 is Optiblanc SPL10® from 3V Sigma

Perfume encapsulate is a core-shell melamine formaldehyde perfume microcapsules

Photobleach is a sulfonated zinc phthalocyanine

Polishing enzyme is Para-nitrobenzyl esterase, reported as 1000 mg active/g

Polyetheramine as described in present disclosure.

Polymer 1 is $bis((C_2H_5O)(C_2H_4O)_n)(CH_3)-N^+-C_xH_{2x}-N^+-(CH_3)-bis((C_2H_5O)(C_2H_4O)_n)$, wherein n=20-30, x=3 to 8 or sulphated or sulfonated variants thereof Polymer 2 is ethoxylated ($EO_{15}$) tetraethylene pentamine Polymer 3 is ethoxylated polyethylenimine Polymer 4 is ethoxylated hexamethylene diamine Polymer 5 is Acusol 305, provided by Rohm & Haas Polymer 6 is a polyethylene glycol polymer grafted with vinyl acetate side chains, provided by BASF.

Protease 1 is Purafect Prime®, 40.6 mg active/g

Protease 2 is Savinase®, 32.89 mg active/g

Protease 3 is Purafect®, 84 mg active/g

Quaternary ammonium is $C_{12\text{-}14}$ Dimethylhydroxyethyl ammonium chloride S-ACMC is Reactive Blue 19 Azo-CM-Cellulose provided by Megazyme Soil release agent is Repel-o-tex® SF2, supplied by Solvay Structurant is Hydrogenated Castor Oil Violet DD is a thiophene azo polymeric hueing dye provided by Milliken The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleaning composition comprising from 1 to 80 wt % of a surfactant system comprising anionic surfactant, an amylase enzyme and a glycosyl hydrolase enzyme having glycoside hydrolase activity, said glycosyl hydrolase enzyme comprises:

(i) a first glycosyl hydrolase enzyme from the endo-alpha-1,4-polygalactosminidase class (EC 3.2.1.109) of enzymes, wherein the first glycoside hydrolase enzyme is a variant having at least 90% identity to SEQ ID NO: 1;

(ii) a second glycosyl hydrolase enzyme from glycoside hydrolase family GH 39, wherein the second glycoside hydrolase enzyme is a variant having at least 90% identity to SEQ ID NO: 13; and (iii) mixtures thereof.

2. The cleaning composition of claim 1, wherein the first glycoside hydrolase enzyme is a variant having at least 95% identity to SEQ ID NO: 1.

3. The cleaning composition of claim 1, wherein the first glycoside hydrolase enzyme is selected from glycoside hydrolases in GH family 114.

4. The cleaning composition of claim 1, wherein the first glycoside hydrolase is PelAh.

5. The cleaning composition of claim 1, wherein the second glycoside hydrolase enzyme is a variant having at least 95% identity to SEQ ID NO: 13.

6. The cleaning composition of claim 1, wherein the second glycoside hydrolase is PslGh.

7. The cleaning composition of claim 1, wherein the glycoside hydrolase enzyme is obtainable from *Pseudomonas*.

8. The cleaning composition of claim 1, wherein the glycoside hydrolase enzyme is an isolated glycoside hydrolase.

9. The cleaning composition of claim 1, wherein the composition further comprises additional enzyme selected from galactanases, mannanases, nucleases, and mixtures thereof.

10. The cleaning composition of claim 9, wherein the composition additionally comprises a deoxyribonuclease enzyme.

11. The cleaning composition of claim 1, wherein the composition further comprises one or more additional enzymes selected from the group comprising lipases, proteases, pectate lyases, cellulases, cutinases, and mixtures thereof.

12. The cleaning composition of claim 1, wherein the composition further comprises a (5-N-acetylglucosaminidase enzyme from E.C. 3.2.1.52 having at least 95% identity to SEQ ID NO: 12.

13. The cleaning composition of claim 1, wherein the surfactant system comprises an anionic and a nonionic surfactant.

14. The cleaning composition of claim 13, wherein the weight ratio of the anionic to nonionic surfactant is from 25:1 to 1:2.

15. The cleaning composition of claim 13, wherein the anionic surfactant is selected from alkyl benzene sulphonates and (optionally alkoxylated) alkyl sulfates and mixtures thereof.

16. A method of cleaning a surface, comprising:
mixing the cleaning composition of claim 1 with water to form an aqueous liquor; and
contacting the surface with the aqueous liquor,
wherein the glycoside hydrolase enzyme is present in the aqueous liquor in an amount of from 0.01 ppm to 1000 ppm enzyme of active protein.

* * * * *